(12) United States Patent
Hibino et al.

(10) Patent No.: US 7,829,547 B2
(45) Date of Patent: Nov. 9, 2010

(54) METHOD AND PHARMACEUTICAL COMPOSITION FOR TREATING PSORIASIS, SQUAMOUS CELL CARCINOMA AND/OR PARAKERATOSIS BY INHIBITING EXPRESSION OF SQUAMOUS CELL CARCINOMA-RELATED ANTIGEN

(75) Inventors: Toshihiko Hibino, Yokohama (JP); Jotaro Nakanishi, Yokohama (JP); Chika Katagiri, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 255 days.

(21) Appl. No.: 11/886,475

(22) PCT Filed: Sep. 22, 2005

(86) PCT No.: PCT/JP2005/018074
§ 371 (c)(1),
(2), (4) Date: Sep. 17, 2007

(87) PCT Pub. No.: WO2006/100797
PCT Pub. Date: Sep. 28, 2006

(65) Prior Publication Data
US 2009/0123572 A1 May 14, 2009

(30) Foreign Application Priority Data
Mar. 18, 2005 (JP) ............................. 2005-080566

(51) Int. Cl.
*A61K 30/71* (2006.01)
*C07H 21/02* (2006.01)
*C07H 21/04* (2006.01)
*C12Q 1/68* (2006.01)

(52) U.S. Cl. .......................... 514/44 A; 435/6; 435/375; 536/23.1; 536/24.1; 536/24.5

(58) Field of Classification Search ........................ None
See application file for complete search history.

(56) References Cited

U.S. PATENT DOCUMENTS

2004/0259247 A1* 12/2004 Tuschl et al. ................. 435/375
2005/0215509 A1* 9/2005 Katagirl et al. ............... 514/44

FOREIGN PATENT DOCUMENTS

WO  WO 03/100059 A2  12/2003
WO  WO 2004/072284 A1  8/2004

OTHER PUBLICATIONS

Suminami et al., Cancer Research vol. 61:1776-1780, 2001.*
Katagiri et al., Increased expression of squamous cell carcinoma antigen protects keratinocytes from UVinduced cell death: critical role of SCCA as a natural inhibitor of the stress kinase JNK/SAPK. *J. Invest. Dermatol.* 122(3), A70, Abstract 417 (2004).

Takeda, A. et al., "Overexpression of Serpin Squamous Cell Carcinoma Antigens in Psoriatic Skin," *Journal of Investigative Dermatology*, Jan. 2002, pp. 147-154, vol. 118, No. 1.

Suminami, Y., et al., "Suppression of a Squamous Cell Carcinoma (SCC)- related Serpin, SCC Antigen, Inhibits Tumor Growth with Increased Intratumor Infiltration of Natural Killer Cells," *Cancer Research*, Mar. 1, 2001, pp. 1776-1780, 61(5).

Suminami, Y., "Tumor-associated ov-serpin, SCC Antigen, is involved in apoptosis," *Bulletin Yamaguchi Medical School*, 2001, pp. 25-27, vol. 48, No. 3-4.

Hamanaka, S., et al., "Serum Level of Squamous Cell Carcinoma Antigen as a New Indicator of Disease Activity in Patients with Psoriasis," *Archives of Dermatology*, Mar. 1997, pp. 393-395, vol. 133, No. 3.

*Experimental Medicine* 18(12):172-180 (2000) (Abstract only), Ohtsu et al.

Supplementary European Search Report mailed Apr. 26, 2010, in EP 05787935.5, 4 pages.

Greaves et al., "Treatment of Psoriasis," New England Journal of Medicine, Mar. 2, 1995, 332(9):581-588.

Katagiri et al., "Novel UV protection mechanism in human skin: role of SCCA in UV-induced cell death," Journal of Dermatological Science, Apr. 2004, 34(2):126, abstract 044.

Katagiri et al., "Serpin squamous cell carcinoma antigen inhibits UV-induced apoptosis via suppression of c-JUN $NH_2$-terminal kinase," Journal of Cell Biology, Mar. 2006, 172(7):983-990.

White et al., "Antisense oligonucleotide treatments for psoriasis," Expert Opinion on Biological Therapy, Jan. 1, 2004, 4(1):75-81.

Wraight et al., "Reversal of epidermal hyperproliferation in psoriasis by insulin-like growth factor I receptor antisense oligonucleotides," Nature Biotechnology, May 2000, 18(5):521-526.

*Experimental Medicine* 18(12):172-180 (2000) (Abstract only) Ohtsu et al.

Katagiri et al., Increased expression of squamous cell carcinoma antigen protects keratinocytes from UVinduced cell death: critical role of SCCA as a natural inhibitor of the stress kinase JNK/SAPK. *J. Invest. Dermatol.* 122(3), A70, Abstract 417 (2004).

* cited by examiner

*Primary Examiner*—Sean R McGarry
(74) *Attorney, Agent, or Firm*—Foley & Lardner LLP

(57) ABSTRACT

In a first aspect thereof, the present invention provides a method for treatment and/or prevention of a disease selected from the group consisting of psoriasis and squamous cell carcinoma by inhibiting the expression of squamous cell carcinoma antigen (SCCA) by cells. In another aspect thereof, the present invention provides a method for screening for substances that inhibit epidermal parakeratosis, wherein the activity of a candidate substance that inhibits cysteine protease inhibitory activity possessed by squamous cell carcinoma antigen 1 (SCCA-1) is used as an indicator.

1 Claim, 13 Drawing Sheets

Fig.7
A
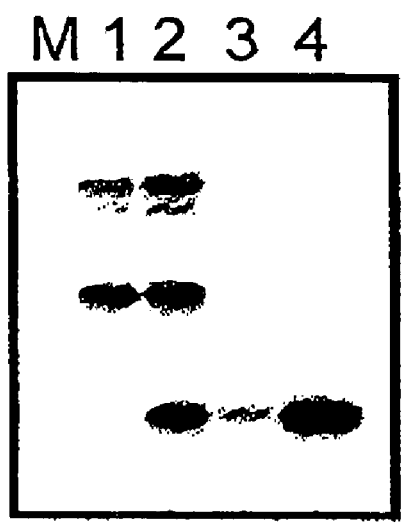
H99 ANTIBODY
B
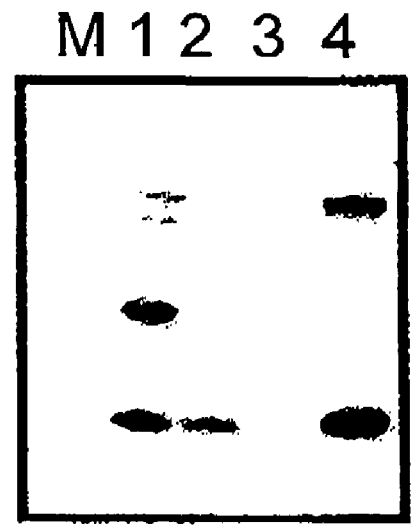
h14D$^{146}$ ANTIBODY

Fig.10
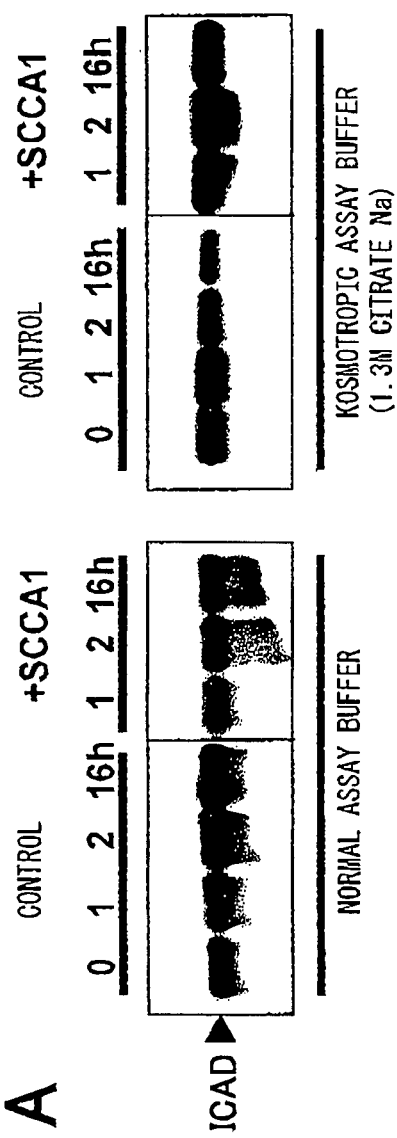
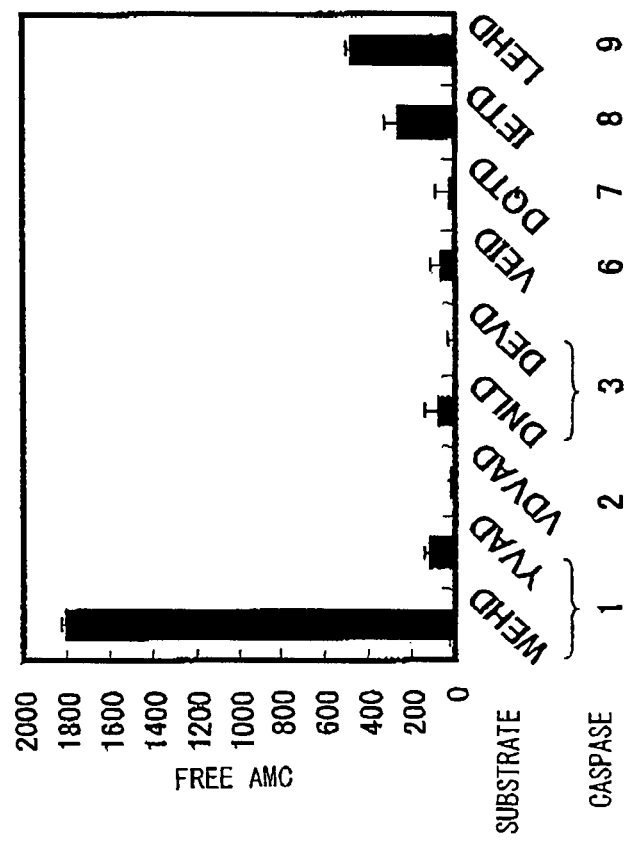
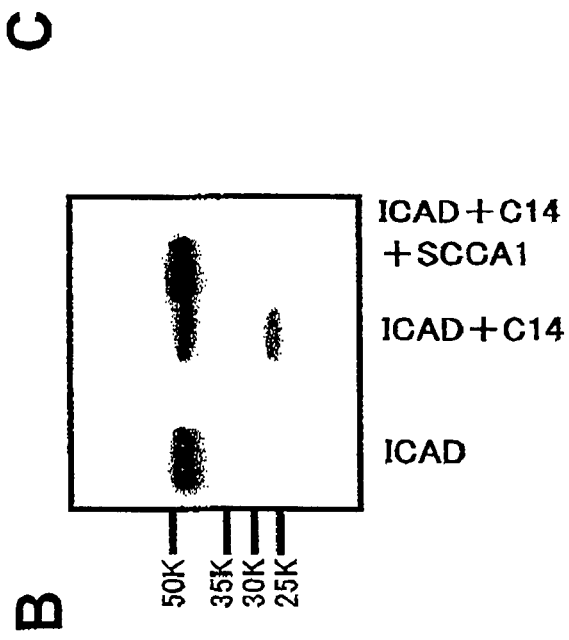

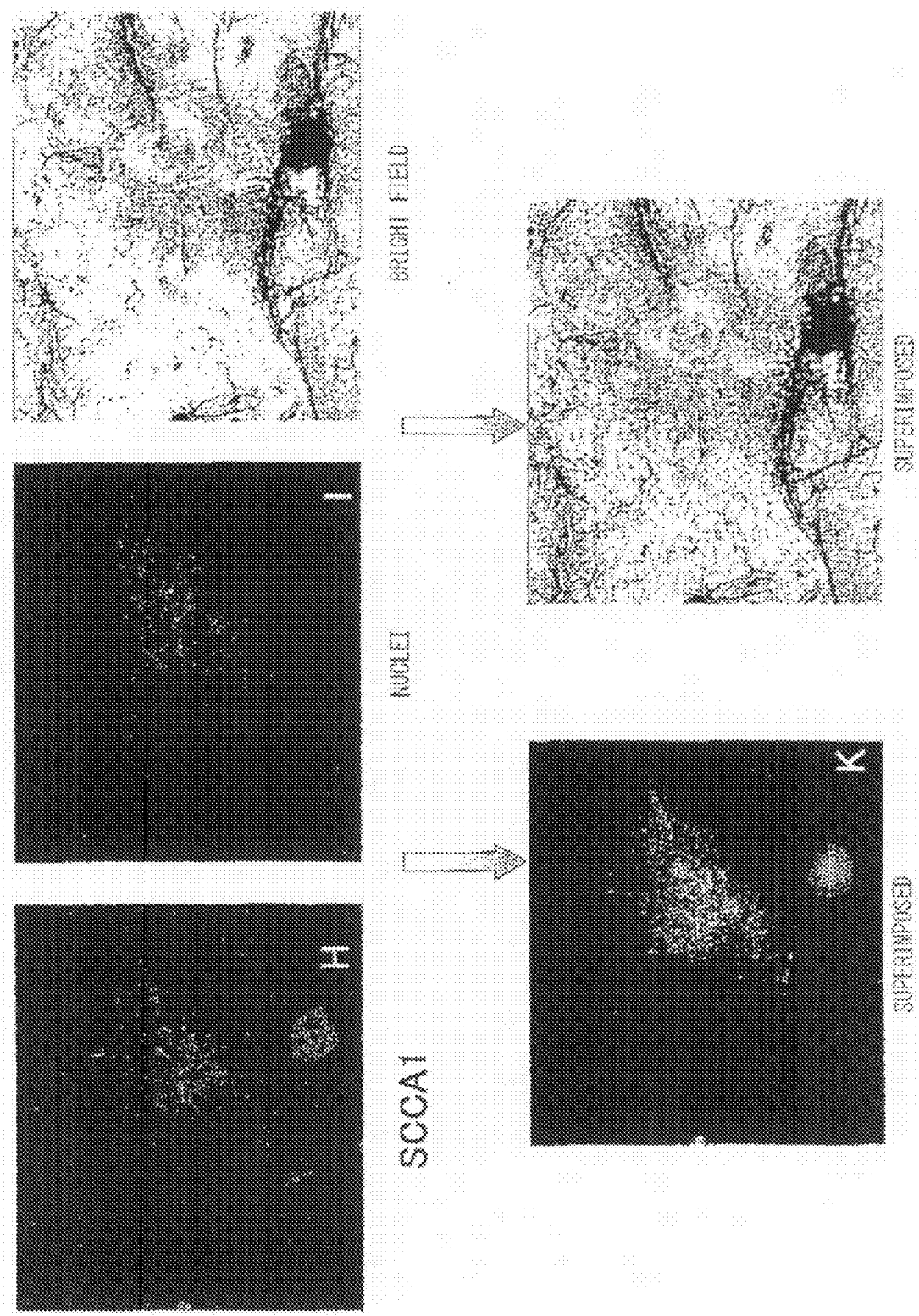

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: SiRNA Target Sequence

<400> SEQUENCE: 1
acatgaactt ggtgttggct t                                        21

<210> SEQ ID NO 2
<211> LENGTH: 21
<212> TYPE: DNA
<213> ORGANISM: Artificial Sequence
<220> FEATURE:
<223> OTHER INFORMATION: SiRNA Target Sequence

<400> SEQUENCE: 2
aagccaacac caagttcatg t                                        21

<210> SEQ ID NO 3
<211> LENGTH: 17
<212> TYPE: DNA
<213> ORGANISM: Artificial Sequence
<220> FEATURE:
<223> OTHER INFORMATION: Forward Primer

<400> SEQUENCE: 3
gtgctatctg gagtcct                                             17

<210> SEQ ID NO 4
<211> LENGTH: 16
<212> TYPE: DNA
<213> ORGANISM: Artificial Sequence
<220> FEATURE:
<223> OTHER INFORMATION: Reverse Primer
```

<400> SEQUENCE: 4
ctgttgttgc cagcaa                                                    16

<210> SEQ ID NO 5
<211> LENGTH: 17
<212> TYPE: DNA
<213> ORGANISM: Artificial Sequence
<220> FEATURE:
<223> OTHER INFORMATION: Taq Man Probe

<400> SEQUENCE: 5
catcacctac ttcaact                                                   17

<210> SEQ ID NO 6
<211> LENGTH: 23
<212> TYPE: DNA
<213> ORGANISM: Artificial Sequence
<220> FEATURE:
<223> OTHER INFORMATION: Forward Primer

<400> SEQUENCE: 6
ctctgcttcc tctaggaaca cag                                            23

<210> SEQ ID NO 7
<211> LENGTH: 20
<212> TYPE: DNA
<213> ORGANISM: Artificial Sequence
<220> FEATURE:
<223> OTHER INFORMATION: Reverse Primer

<400> SEQUENCE: 7
tgttggcgat cttcagctca                                                20

<210> SEQ ID NO 8
<211> LENGTH: 21
<212> TYPE: DNA
<213> ORGANISM: Artificial Sequence
<220> FEATURE:
<223> OTHER INFORMATION: Taq Man Probe

<400> SEQUENCE: 8
agttccagat cacatcgagt t                                              21

<210> SEQ ID NO 9
<211> LENGTH: 19
<212> TYPE: DNA
<213> ORGANISM: Artificial Sequence
<220> FEATURE:
<223> OTHER INFORMATION: Forward Primer

<400> SEQUENCE: 9
gaaggtgaag gtcggagtc                                                 19

<210> SEQ ID NO 10
<211> LENGTH: 20
<212> TYPE: DNA
<213> ORGANISM: Artificial Sequence
<220> FEATURE:
<223> OTHER INFORMATION: Reverse Primer

<400> SEQUENCE: 10
gaagatggtg atgggatttc                                                20

<210> SEQ ID NO 11

```
<211> LENGTH: 22
<212> TYPE: DNA
<213> ORGANISM: Artificial Sequence
<220> FEATURE:
<223> OTHER INFORMATION: Taq Man Probe

<400> SEQUENCE: 11
aggctgagaa cgggaagctt gt                                              22

<210> SEQ ID NO 12
<211> LENGTH: 65
<212> TYPE: DNA
<213> ORGANISM: Artificial Sequence
<220> FEATURE:
<223> OTHER INFORMATION: Sense Oligonucleotide for SiRNA

<400> SEQUENCE: 12
gatcccggcc aacaccaagt tcatgtttca agagaacatg aacttggtgt tggcttttt      60 ggaaa                                                                 65

<210> SEQ ID NO 13
<211> LENGTH: 65
<212> TYPE: DNA
<213> ORGANISM: Artificial Sequence
<220> FEATURE:
<223> OTHER INFORMATION: Antisense Oligonucleotide for SiRNA

<400> SEQUENCE: 13
agcttttcca aaaagccaa caccaagttc atgttctctt gaaacatgaa cttggtgttg      60
gccgg                                                                 65

<210> SEQ ID NO 14
<211> LENGTH: 32
<212> TYPE: DNA
<213> ORGANISM: Artificial Sequence
<220> FEATURE:
<223> OTHER INFORMATION: Forward Primer

<400> SEQUENCE: 14
aaggatccaa tccgcggtct ttggaagagg ag                                   32

<210> SEQ ID NO 15
<211> LENGTH: 39
<212> TYPE: DNA
<213> ORGANISM: Artificial Sequence
<220> FEATURE:
<223> OTHER INFORMATION: Reverse Primer

<400> SEQUENCE: 15
tttctgcagg ttgcagatac agccgtttcc ggagggtgc                            39
```

METHOD AND PHARMACEUTICAL COMPOSITION FOR TREATING PSORIASIS, SQUAMOUS CELL CARCINOMA AND/OR PARAKERATOSIS BY INHIBITING EXPRESSION OF SQUAMOUS CELL CARCINOMA-RELATED ANTIGEN

TECHNICAL FIELD

The present invention provides a method and pharmaceutical composition for treating and/or preventing a disease selected from the group consisting of psoriasis and squamous cell carcinoma by inhibiting expression of squamous cell carcinoma antigen (SCCA) by cells. In addition, the present invention provides a method for screening substances that inhibit epidermal parakeratosis based on the activity of candidate substances that inhibits cysteine protease activity possessed by squamous cell carcinoma antigen 1 (SCCA-1), a substance that inhibits epidermal parakeratosis screened by such a method, and a method for inhibiting epidermal parakeratosis that normalizes keratization of epidermal cells by inhibiting caspase-14 inhibitory activity of SCCA-1 in epidermal cells.

BACKGROUND ART

SCCA is an antigen extracted from squamous epithelial cells that demonstrates high concentrations in blood obtained from patients suffering from squamous cell carcinoma of the cervix, lungs, esophagus and skin and is frequently used to diagnosis squamous cell carcinoma (H. Kato et al., Cancer, 40: 1621-1628 (1977); N. Mino et al., Cancer, 62: 730-734 (1988)). Since SCCA levels in the blood demonstrate a favorable correlation with such factors as the progressive stage of squamous cell carcinoma, degree of malignancy and tumor size in particular, it is a particularly effective marker not only for early detection of cancer but also for evaluating the effects of cancer treatment and diagnosing the risk of recurrence.

In addition, increased expression of SCCA is also known to be observed in the upper layer of psoriatic epidermis (Takeda A. et al., J. Invest. Dermatol. (2002) 118(1), 147-154). Psoriasis is a type of skin disease in the form of chronic and recurrent inflammatory parakeratosis characterized by abnormal proliferation and differentiation of epidermal cells and infiltration by inflammatory cells. Psoriasis is believed to occur due to genetic factors in addition to various environmental factors (Hopso-Havu et al., British Journal of Dermatology (1983) 109, 77-85).

SCCA is encoded by two genes SCCA-1 and SCCA-2 arranged in tandem on chromosome 18q21.3. The proteins SCCA-1 and SCCA-2 encoded by these genes both have a molecular weight of about 45,000, and although they have an extremely high degree of homology, since they have different amino acid sequences at the reaction site, they are believed to have different functions (Schick et al., J. Biol. Chem. (1997) 27231, 1849-55). Although SCCA-1 and SCCA-2 are known to be highly expressed in diseases such as squamous cell carcinoma and psoriasis, it is unclear as to what functions they perform in diseased cells.

On the other hand, keratinocytes are known to have the function of forming a protective barrier referred to as the "cornified layer" against harmful environments as a result of terminal differentiation. The terminal differentiation process is accurately controlled by a differentiation program, and begins with proliferative basal cells, goes through the stages of prickle cells, granular cells and finally ends with the differentiation into keratinocytes. Dramatic changes occur both inside and outside the keratinocytes during the transition period from granular cells to keratinocytes. The keratinocytes lose their nucleus and cellular organelles, while acquiring a peripheral lipid layer, a strengthened cell membrane referred to as cornified integument, and a keratin pattern. The keratin pattern maintains a flexible and tight internal structure. According to previous reports, keratinocytes undergoing differentiation demonstrate characteristics of apoptosis such as DNA fragmentation and TUNEL-positive cells (Haake A. R., J. Invest. Dermatol., 101, 107-12 (1993)). Caspase-like activity has been detected in extracts of human keratinocytes, and several types of caspases are expressed in human keratinocytes. However, other reports have indicated that typical pro-apoptotic caspases such as caspase-3, caspase-6 and caspase-7 are not activated at the time of terminal differentiation. Differentiation abnormalities frequently lead to the permanent presence of nuclei in the cornified layer referred to as "parakeratosis". Parakeratosis causes serious damage to the barrier function of the skin. However, it has yet to be determined as to which factors are involved in the denucleation process, and the manner in which this process is regulated during keratinocyte differentiation.

Caspases are well-known apoptotic cell death execution factors, and are cysteine proteases preserved in the evolutionary process that cleave substrates after aspartic acid residues. Caspases in mammals are divided into three subgroups according to their structure and function, namely initiator caspase, effector caspase and inflammatory caspase. Effector caspase fulfills the important role of decomposing the inhibitor ICAD of CAD (caspase activated DNase), resulting in the dissociation of CAD as an active nuclease (Enari M. et al., Nature, 391, 43-50 (1998)). Caspase activity is regulated by various molecules. In particular, there are three groups of inhibitory proteins in direct collaboration with several caspases. Baculovirus anti-apoptotic protein p35 inhibits caspases-1, -3, -6, -7, -8 and -10 without acting on serine or other cysteine proteinases (Zhou Q. et al., Biochemistry, 37, 10757-65 (1998)). Baculovirus also synthesizes other anti-apoptotic proteins and inhibitors of apoptosis proteins (IAP). Homologues of IAP are also found in mammals (Verhagen A. M. et al., Genome Biol., 2, Reviews 3009 (2001)). Mammalian IAP blocks apoptosis by inhibiting caspase-14 or by antagonizing pro-apoptosis-promoting factors such as DIABLO/Smac (Wu G., Nature, 408, 1008-12 (2000)). Cytokine response modifier A (Crm A) is a genetic product of cowpox virus that is capable of inhibiting apoptotic caspases and inflammatory caspases (Garcia-Calvo M. et al., J. Biol. Chem., 273, 32608-13 (1998)). It is quite interesting that Crm A has been suggested to belong to a superfamily of serine proteinase inhibitors, and that some serine proteinase inhibitors, such as PI-9 and PAI-1, are able to inhibit apoptosis by interacting with caspase-1 and caspase-3, respectively (Annand R. R. et al., Biochem. J., 342Pt3, 655-65 (1999)). It will therefore be interesting to determine whether or not terminal differentiation of keratinocytes constitutes a portion of apoptosis phenomena, and the manner in which arbitrary regulatory proteins are involved in this process.

Caspase-14 is the newest member of the caspase family, and is expressed nearly exclusively by differentiating keratinocytes. Caspase-14 was identified by an EST homologous among members of the caspase family. According to findings of recent research, the caspase-14 present in keratinocytes is a processed heterodimer that demonstrates enzymatic activity with respect to the synthetic substrate Trp-Glu-His-Asp-AFC corresponding to caspase-1 (Mikolajczyk J. et al., Biochemistry, 43, 10560-9 (2004)). This hydrolysis activity requires protein decomposition and cleavage as well as the presence of a kosmotropic salt. Although the primary structure of caspase-14 is extremely similar to that of inflammatory caspases such as caspase-1, -4 and -5, the expression of caspase-14 limited to differentiated keratinocytes has been suggested to be involved in keratinocyte terminal differentiation in a different mode (Lippens S. et al., Cell Death Differ., 7, 1218-24 (2001)). However, the activation mechanism of caspase-14 along with its natural substrate or regulatory factors have yet to be elucidated.

DISCLOSURE OF THE INVENTION

As a result of conducting research for the purpose of elucidating the physiological mechanism of skin involving SCCA, the inventors of the present invention surprisingly found that SCCA is an anti-apoptotic factor having an action of inhibiting cell apoptosis.

Simply speaking, the inventors of the present invention conducted studies of the UV defense mechanism of the skin, and clearly demonstrated that the expression of SCCA in the spinous layer and granular layer increased prominently due to UV irradiation of human skin. Therefore, when a stable expression system was established by inserting human SCCA-1 and SCCA-2 genes into 3T3 cells not observed to express SCCA, and UV radiation-induced apoptosis was investigated in cells having a stable SCCA expression system, UV radiation-induced apoptosis was clearly demonstrated to decrease significantly in each of the stable SCCA expression systems.

Moreover, as a result of establishing an SCCA-1 and SCCA-2 knockdown (siSCCA) cell line by RNA interference in which siRNA was constitutively expressed with a pSilencer vector in HaCat cells highly expressing SCCA, and then irradiating that cell line with UV light, the apoptosis rate in the SCCA knockdown cells was shown to be significantly higher than a control cell line. On the basis of these findings, the inventors of the present invention concluded that SCCA is a protein that has the action of inhibiting apoptosis.

In diseases such as psoriasis and cancer associated with abnormal cell proliferation and differentiation, cancer cells are believed to escape cell death and continue to proliferate abnormally by inhibiting apoptosis. Thus, it is clear that in cells highly expressing SCCA, SCCA inhibits cell death due to its anti-apoptotic action thereby leading to abnormal proliferation of those cells. Accordingly, it is clear that it would be possible treat and prevent diseases such as squamous cell carcinoma and psoriasis associated with abnormal cell proliferation and the like if it were possible to inhibit the expression of SCCA having apoptosis inhibitory action.

In consideration of these findings, an object of the present invention is to provide a method and pharmaceutical composition for treating and preventing diseases associated with abnormal proliferation of SCCA highly expressing cells, and particularly squamous cell carcinoma and psoriasis.

Moreover, an object of the present invention is to develop a means for inhibiting and treating epidermal parakeratosis using a completely novel approach differing from the prior art by elucidating the mechanism of epidermal parakeratosis. When considering that there are no effective drugs for skin diseases such as atopic dermatitis and psoriasis associated with parakeratosis, the present invention is expected to have a considerable effect in the fields of dermatology and cosmetics.

In a first aspect thereof, the present invention provides a method for treatment and/or prevention of a disease selected from the group consisting of psoriasis and squamous cell carcinoma by inhibiting the expression of squamous cell carcinoma antigen (SCCA) by cells. Preferably, inhibition of the expression of SCCA by cells is carried out by RNA interference of a gene encoding SCCA. In a more preferable aspect thereof, the RNA interference uses a double-stranded RNA comprising a sense oligonucleotide strand containing the oligonucleotide of SEQ ID NO. 1 or mutant thereof and an antisense oligonucleotide strand containing the oligonucleotide of SEQ ID NO. 2 or mutant thereof. Here, a mutant of the oligonucleotide of SEQ ID NO. 1 has a sequence that hybridizes under highly stringent conditions with nucleotides at positions 46 to 66 of a gene encoding SCCA, while a mutant of the oligonucleotide of SEQ ID NO. 2 has a sequence that hybridizes under highly stringent conditions with a complementary strand of nucleotides at positions 46 to 66 of a gene encoding SCCA.

In another aspect thereof, the present invention provides a pharmaceutical composition for the treatment and/or prevention of a disease selected from the group consisting of psoriasis and squamous cell carcinoma by inhibiting the expression of SCCA by cells. Preferably, the pharmaceutical composition contains a double-stranded RNA that provides a short strand RNA causing RNA interference with a gene encoding SCCA. In a more preferable aspect thereof, the pharmaceutical composition contains a double-stranded RNA comprising a sense oligonucleotide strand containing the oligonucleotide of SEQ ID NO. 1 or a mutant thereof, and an antisense oligonucleotide strand containing the oligonucleotide of SEQ ID NO. 2 or a mutant thereof. Here, a mutant of the oligonucleotide of SEQ ID NO. 1 has a sequence that hybridizes under highly stringent conditions with nucleotides at positions 46 to 66 of a gene encoding SCCA, while a mutant of the oligonucleotide of SEQ ID NO. 2 has a sequence that hybridizes under highly stringent conditions with a complementary strand of nucleotides at positions 46 to 66 of a gene encoding SCCA.

In a preferable aspect thereof, the double-stranded RNA is in a form of being contained in a vector such as a pSilencer vector.

Moreover, the present invention provides a method for preparing cells in which expression of SCCA has been inhibited. Preferably, inhibition of SCCA expression is carried out by RNA interference of a gene encoding SCCA. In a more preferable aspect thereof, the RNA interference uses a double-stranded RNA comprising a sense oligonucleotide strand containing the oligonucleotide of SEQ ID NO. 1 or mutant thereof and an antisense oligonucleotide strand containing the oligonucleotide of SEQ ID NO. 2 or mutant thereof. Here, a mutant of the oligonucleotide of SEQ ID NO. 1 has a sequence that hybridizes under highly stringent conditions with nucleotides at positions 46 to 66 of a gene encoding SCCA, while a mutant of the oligonucleotide of SEQ ID NO. 2 has a sequence that hybridizes under highly stringent conditions with a complementary strand of nucleotides at positions 46 to 66 of a gene encoding SCCA. Moreover, the present invention provides cells in which expression of SCCA has been inhibited by the method described above and a mammal containing such cells.

Accordingly, the present invention provides a method and pharmaceutical composition for treating and preventing a disease selected from the group consisting of squamous cell carcinoma and psoriasis.

In a still other aspects thereof, the present invention includes the aspects of the invention described below.

[1] A method for screening for substances that inhibit epidermal parakeratosis, wherein the activity of a candidate substance that inhibits cysteine protease inhibitory activity possessed by squamous cell carcinoma antigen 1 (SCCA-1) is used as an indicator.

[2] The method of [1] above, comprising the following assay systems (1), (2) and (3):

(1) measuring cysteine protease activity and obtaining that measured value [x];

(2) i) mixing a candidate compound with an equal amount of the cysteine protease defined in (1) above in terms of enzyme activity followed by incubation; and ii) measuring the cysteine protease activity of the incubated mixture of (2)i) above under the same conditions as (1) above and obtaining that measured value [y]; and, (3) i) mixing the target candidate in an amount equal to that used in (2)i) with SCCA-1 followed by incubation;

ii) mixing the incubated mixture of (3)i) with an equal amount of the cysteine protease defined in (1) above in terms of enzyme activity, and incubating under the same conditions as (2)i) above; and iii) measuring the cysteine protease activity of the incubated mixture of (3)ii) above under the same conditions as (1) above and obtaining that measured value [z]; wherein, the candidate compound is determined to have activity that inhibits cysteine protease inhibitory activity possessed by SCCA-1 and is selected as a substance that inhibits epidermal parakeratosis if it satisfies the following condition:

$$\{[z]/[x] \times 100\} - \{100 - [y]/[x] \times 100\} > 0.$$

[3] The method of [2] above, wherein the condition to be satisfied is $\{[z]/[x] \times 100\} - \{100 - [y]/[x] \times 100\} > 3$.

[4] The method of [3] above, wherein the condition to be satisfied is $\{[z]/[x] \times 100\} - \{100 - [y]/[x] \times 100\} > 16$.

[5] The method of any of [1] to [4] above, wherein the cysteine protease is caspase-14.

[6] The method of any of [1] to (4) above, wherein the cysteine protease is papain.

[7] A skin composition for external use, and particularly an aesthetic skin composition for external use, for inhibiting epidermal parakeratosis containing as an active ingredient thereof one or a plurality of types of herbal medicines selected from the group consisting of cattail extract, grape extract, tomato extract, cucumber extract, kiwi extract and jujube extract.

[8] The skin composition for external use of [7] above containing cattail extract.

[9] The composition of [7] or [8] above, wherein the epidermal parakeratosis is caused by psoriasis.

[10] The composition of [7] or (8) above, wherein the epidermal parakeratosis is caused by atopic dermatitis.

[11] A method for inhibiting epidermal parakeratosis by inhibiting caspase-14 inhibitory activity of SCCA-1 in epidermal cells to normalize epidermal cell keratization.

[12] The method of [11] above, wherein caspase-14 inhibitory activity of SCCA-1 in epidermal cells is inhibited by applying to the skin a skin composition for external use containing as an active ingredient thereof one or a plurality of types of herbal medicines selected from the group consisting of cattail extract, grape extract, tomato extract, cucumber extract, kiwi extract and jujube extract.

[13] The method of [12] above, wherein the skin composition for external use contains cattail extract.

Accordingly, the present invention is able to provide a means for inhibiting and treating epidermal parakeratosis using a completely novel approach differing from the prior art.

[14] The use of one or a plurality of types of herbal medicines selected from the group consisting of cattail extract, grape extract, tomato extract, cucumber extract, kiwi extract and jujube extract as an active ingredient for producing a skin composition for external use, and particularly an aesthetic or cosmetic skin composition for external use, for inhibiting epidermal parakeratosis.

[15] The use of [14] above, wherein the herbal medicine is cattail extract.

[16] The use of [14] or [15] above, wherein the epidermal parakeratosis is caused by psoriasis.

[17] The use of [14] or [15] above, wherein the epidermal parakeratosis is caused by atopic dermatitis.

BRIEF DESCRIPTION OF THE DRAWINGS

FIG. 7 shows a Western blot analysis of a skin extract. The presence of zymogen and active caspase-14 by immunoblotting using H-99 antibody and h14D$^{146}$ antibody. 10 μg (Lanes 1, 2 and 4) and 1 μg (Lane 3) of whole skin extract, skin equivalent extract and keratinocyte extract were applied.

FIG. 10 (A) shows the cleavage activity of purified caspase-14 against ICAD. (B) shows a Western blot analysis using FL331 antibody. Cleavage products were observed at 33 and 27 KDa. ICAD cleavage was completely inhibited by pre-incubating using 10 μM SCCA-1. ICAD decomposition was only observed in the presence of kosmotropic salt. Western blot analysis using an antibody specific for the amino terminal demonstrated a loss of intact ICAD molecules during extended incubation with caspase-14. When SCCA-1 was added to the mixture, ICAD decomposition was virtually not detected, and there were still no effects after incubating for 16 hours (B). (C) The results are shown of investigating hydrolysis activity on synthetic caspase substrates in the presence of kosmotropic salt.

FIG. 13 shows co-localization of SCCA-1 and parakeratotic nuclei. Hardly any SCCA-1 was able to be detected in sections of normal skin. SCCA-1-positive sites were observed in the superficial layer of the skin of AD patients (H). Nuclear clusters were only observed at these sites (I). The bright field image is shown in (J). Superimposed images indicated that SCCA-1-positive sites are preferably superimposed with sites where undigested nuclei are present (K). SCCA-1 staining and a different superimposed image corresponding to bright field observation are also shown (L).

BEST MODE FOR CARRYING OUT THE INVENTION

Figure 1:
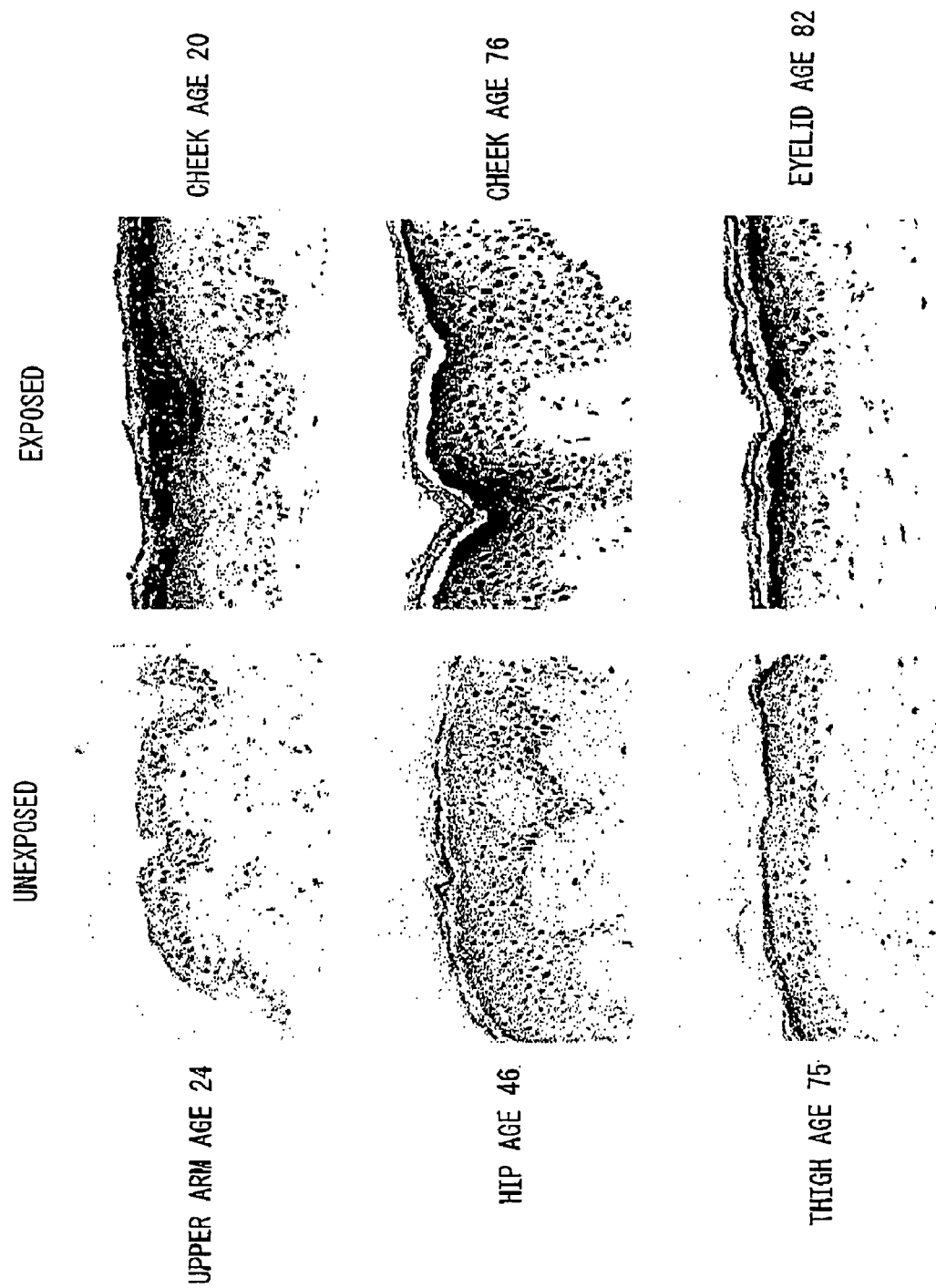
FIG. 1 shows the expression of SCCA in epidermis at exposed sites and unexposed sites.

Method and Pharmaceutical Composition for Treating Psoriasis and/or Squamous Cell Carcinoma The inventors of the present invention clearly demonstrated that SCCA is a protein that has action which inhibits apoptosis. Thus, it is clear that inhibition of the expression of SCCA would make it possible to treat and prevent diseases associated with abnormal proliferation and differentiation of cells expressing squamous cell carcinoma antigen. Examples of squamous cell carcinoma include squamous cell carcinoma of organs such as the cervix, lungs, esophagus, maxilla and skin.

SCCA is a protein having a molecular weight of about 45,000 that is present in squamous cell carcinoma cells and psoriatic epidermis as previously described. The amino acid sequences of SCCA-1 and SCCA-2 along with the nucleic acid sequences that encode them have been described by Takeda et al., J. Invest. Dermatol., 118, 147-154 (2002) (op cit).

Although inhibition of expression of SCCA by cells can be achieved by various genetic technologies such as RNA interference, antisense RNA-DNA methods, peptide and RNA-DNA aptamers, site-specific deletion, homologous recombination, dominant-negative alleles and intrabodies, RNA interference is particularly preferable.

RNA interference is a method used to inhibit expression of a target gene by inserting into cells double-stranded RNA composed of a strand containing a sense oligonucleotide of about 21 to 23 base pairs complementary to a portion of mRNA encoding a portion of the target gene, and a strand containing an antisense oligonucleotide of about 21 to 23 base pairs homologous to a portion of that mRNA. This method is based on the interference characteristics of double-stranded RNA derived from a gene-coding region, and has been demonstrated to have superior usefulness in genetic research on nematodes (Fire et al., Nature (1998) 391: 806-811). It can also be used to produce function deficient phenotypes in fruit flies and mammals.

In the method of the present invention, double-stranded RNA (dsRNA) is synthesized in vitro composed of a sequence complementary to a suitable target region of SCCA gene, and preferably a region having a nucleotide length of about 18 to 23 nucleotides (sense oligonucleotide), and a sequence having a nucleotide length of about 18 to 23 nucleotides homologous to that sense sequence (antisense oligonucleotide). Preferably, the double-stranded RNA is composed of a sense oligonucleotide containing a sequence complementary to the nucleotides at positions 46 to 66 of SCCA gene (ACATGAACTT GGTGTTGGCT T: SEQ ID NO. 1), and an antisense oligonucleotide containing a sequence homologous to the sequence of nucleotides at positions 46 to 66 (AAGCCAACAC CAAGTTCATG T: SEQ ID NO. 2). Although there are no particular limitations on the total lengths of the sense and antisense oligonucleotides, the lengths are, for example, about 25 to 100 nucleotides, preferably 40 to 80 nucleotides and more preferably 50 to 70 nucleotides.

The sense oligonucleotide may be an oligonucleotide containing a mutant of the oligonucleotide of SEQ ID NO. 1. This mutant preferably has a sequence that hybridizes under high stringent conditions with nucleotides at positions 46 to 66 of a gene encoding SCCA. In addition, the antisense oligonucleotide preferably has a sequence that hybridizes under highly stringent conditions with a complementary strand to nucleotides at positions 46 to 66 of a gene encoding SCCA. Here, hybridization under highly stringent conditions refers to conditions including a sodium concentration of about 10 to 40 mM and preferably about 20 mM, and a temperature of about 50 to 70° C. and preferably about 60 to 65° C.

The resulting double-stranded RNA may be inserted directly into target cells or may be inserted into target cells after linking dsRNA to a vector having a required element for transcription such as a promoter or terminator. Although various vectors known among persons with ordinary skill in the art can be used for the vector, the pSilencer vector (Ambion) is preferable. As a result of inserting a vector containing the double-stranded RNA into cells, the sense strand of SEQ ID NO. 1 (or mutant thereof), the antisense strand of SEQ ID NO. 2 (or mutant thereof), and short hairpin RNA (shRNA) that connects the sense strand and antisense strand are formed by transcription within the cells. The shRNA is then cleaved to a short strand RNA (short interfering RNA) of about 21 to 23 base pairs by intracellular nuclease and dicer, and forms an RISC complex that causes RNA interference that cleaves SCCA mRNA resulting in inhibition of the expression of SCCA by the inserted cells.

Preferably, in the present invention, a gene that inhibits expression of SCCA, such as a gene that inhibits expression of the double-stranded RNA or other SCCA, including antisense DNA or RNA and aptamer RNA or DNA (to be simply referred to as an "SCCA expression-inhibiting gene"), is used as an active ingredient of a pharmaceutical composition for inhibiting expression of SCCA, thereby preventing and/or treating psoriasis or squamous cell carcinoma. This SCCA expression-inhibiting gene may be administered directly by injection, or may be administered to an affected area by a method consisting of administration of a vector or plasmid incorporating that gene.

Examples of the aforementioned vector include adenovirus vector, adeno-associated virus vector, herpes virus vector, vaccinia virus vector and retrovirus vector, and the use of these vectors enables the SCCA expression-inhibiting gene to be administered efficiently. In addition, a method can also be employed by which the SCCA expression-inhibiting gene is inserted into liposomes or other phospholipid vesicles followed by administration of the liposomes. Since liposomes are closed vesicles containing biodegradable material, mixing liposomes and genes causes the gene to be retained in the aqueous layer and lipid bimolecular layer within the liposomes (liposome-gene complex). Next, culturing this complex with cells results in the gene within the complex being taken up into the cells (lipofection). The resulting cells may be administered by an administration method described below.

The aforementioned pharmaceutical composition can be administered in an administration form consisting of systemic administration such as ordinary intravenous or intraarterial administration, or local administration into various tissues in which a tumor or psoriasis is present. Moreover, an administration form can also be used that combines a catheter procedure, surgical procedure and the like. The dosage of the pharmaceutical composition of the present invention varies according to age, gender, symptoms, administration route, number of administrations and drug form, and is suitably determined by a physician and the like.

When plasmid DNA is administered directly into a vein, it is difficult to express a gene since the DNA is immediately decomposed by enzymes such as DNase in the blood. Therefore, in the case of using plasmid DNA, it is preferably to use a method by which the plasmid is injected directly. Since this method allows the vector to be purified more easily as compared with methods using vial vectors, a large amount can be prepared in a short period of time, thereby offering various advantages such as being produce a large amount in a short period of time and the absence of restrictions on size of the inserted gene or concentration at the time of injection (Verma, I. M. et al., Nature 389: 239-242, 1997).

In the case of a DNA direct injection method, the purified plasmid DNA may be dissolved in physiological saline and the like followed by injecting directly into muscle. As a result, the plasmid DNA is taken up into the cells in the vicinity of the injection site, expression of the incorporated gene occurs in expression units of the eukaryote of the plasmid, and the gene product is produced. Although DNA direction injection methods currently consist mainly of intramuscular injection, plasmid DNA can also be directly injected into, for example, tumors (Yang, P. J. et al., Gene. Ther. 3: 542-548, 1996), or into the skin (Hengge, U. R. et al., J. Clin. Invest. 97: 2911-2916, 1996; Choate, K. A. et al., Hum. Gene. Ther. 8: 1659-1665, 1997).

Intramuscularly injected plasmid DNA is injected by dissolving, for example, 1 μg to 1 mg, and preferably 25 to 100 μg of DNA in 50 μl of physiological saline. This enables the maximum level of expression to be obtained after 4 to 7 days.

Confirmation of inhibition of SCCA expression can be carried out by, for example, directly measuring the amount of SCCA in cells. Preferably, this is determined by extracting RNA from the cells and measuring the amount of RNA that encodes SCCA. Extraction of RNA and measurement of the amount thereof are known in the art, and quantification of RNA, for example, can be carried out by quantitative polymerase chain reaction (PCR). In addition, measurement of SCCA can be carried out by various methods known method in the art by utilizing specific antibody to SCCA, examples of which include immunostaining methods using a fluorescent substance, pigment or enzyme, Western blotting, or immunoassay methods such as ELISA or RIA. The expressed amount of SCCA can also be measured by measuring a known biological activity of SCCA. In addition, expression of SCCA can also be determined through in situ hybridization or measurement of other biological activity.

The cells in which expression of SCCA is inhibited by the present invention are preferably epidermal cells, and may be granular cells or spinous cells. In addition, mammals having such cells may be humans or non-human mammals such as mice, rats, hamsters, guinea pigs, rabbits, dogs, cats, horses, cows, sheep, pigs, goats or monkeys. The mammals and cells as claimed in the present invention can be used as model animals or cells used in, for example, the elucidation of the UV defense mechanism of the epidermis, or research, development and screening of drugs preventing or inhibiting UV-induced skin damage.

Screening Method for Substances Inhibiting Parakeratosis, Substances Screened by this Method, and Method for Inhibiting Parakeratosis Psoriasis is a type of skin disease in the form of a chronic, recurrent inflammatory parakeratosis characterized by abnormal proliferation and differentiation of epidermal cells and infiltration by inflammatory cells. Psoriasis is believed to occur due to genetic factors in addition to various environmental factors (Hopso-Havu et al., British Journal of Dermatology (1983) 109, 77-85). SCCA is encoded by two genes SCCA-1 and SCCA-2 arranged in tandem on chromosome 18q21.3. The proteins SCCA-1 and SCCA-2 encoded by these genes both have a molecular weight of about 45,000, and although they have an extremely high degree of homology, since they have different amino acid sequences at the reaction site, they are believed to have different functions (Schick et al., J. Biol. Chem. (1997) 27231, 1849-55).

The screening method for substances inhibiting parakeratosis as claimed in the present invention uses as an indicator the activity of a candidate substance that inhibits cysteine protease inhibitory activity possessed by SCCA-1. Although it is ideally most preferable to use caspase-14 for the cysteine protease, other members of the caspase family, or in consideration of ease of acquisition, any other known type of cysteine protease such as papain, cathepsins such as cathepsin B or cathepsin L, bromelain or ficin, can be used as a substitute.

In a preferable aspect thereof, the aforementioned screening method is composed of (1) a system for assaying the activity of cysteine protease, (2) a system for assaying the activity of cysteine protease in the presence of a candidate substance only, and (3) a system for pre-incubating a candidate substance and SCCA-1 and assaying the activity of cysteine protease in the presence of the incubated mixture. Assay system (2) makes it possible to determine the effects of the candidate substance on cysteine protease. Furthermore, there are no particular limitations on the order in which assay systems (1), (2) and (3) are carried out, and the assays may be carried out on the same day or different days provided the assay conditions are the same.

Measurement of the enzymatic activity of cysteine protease can be carried out by a method known among persons with ordinary skill in the art using a commonly used cysteine protease substrate such as Nα-benzoyl-L-arginine 4-nitroanilide hydrochloride (L-BAPNA).

In a particularly preferable aspect thereof, this screening method can be carried out in the manner described below.

(1) System for Assaying Cysteine Protease Activity

Cysteine protease is incubated for a predetermined amount of time in a suitable assay buffer such as HEPES buffer. Next, a cysteine protease substrate such as L-BAPNA is added, and after incubating for a predetermined amount of time at a predetermined temperature, color is developed followed by measurement of the enzyme activity [x] of cysteine protease.

(2) System for Assaying Cysteine Protease Activity in the Presence of a Candidate Substance Only After incubating the aforementioned assay buffer and candidate substance for a predetermined amount of time, cysteine protease is added followed by measurement of cysteine protease activity under the same conditions as (1). The percentage (%) of this cysteine protease enzyme activity [y] to the aforementioned (x) is determined by $\{[y]/[x]\times 100\}$.

The value of $\{[y]/[x]\times 100\}$ is an indicator of the cysteine protease inhibitory activity possessed by a test substance as described above, or in other words, the closer that value is to 100, the lower the cysteine protease inhibitory activity of the test substance. In addition, the value obtained by subtracting the value $\{[y]/[x]\times 100\}$ from 100, namely $\{100-[y]/[x]\times 100\}$ is also determined. In this case, the closer this value is to 0, the lower the cysteine protease inhibitory activity of the test substance.

(3) Measurement of Enzyme Activity in a System Containing SCCA-1, Candidate Substance and Cysteine Protease The aforementioned assay buffer and SCCA-1 are mixed followed by addition of a candidate substance and incubating for a predetermined amount of time. Cysteine protease activity [z] is then measured under the conditions of (1) or (2). The percentage (%) of this cysteine protease enzyme activity [z] to the aforementioned [x] is determined by $\{[z]/[x]\times 100\}$.

This value of $\{[z]/[x]\times 100\}$ is an indicator of the total of the cysteine protease inhibitory activity of SCCA-1 and the cysteine protease inhibitory activity of the test substance itself, or in other words, the closer this value is to 100, the lower the total inhibitory activity.

Finally, the value obtained by subtracting the value of $\{100-[y]/[x]\times 100\}$ from the value of $\{[z]/[x]\times 100\}$ is determined. The larger this difference, the lower the cysteine protease inhibitory activity of SCCA-1 in the system containing SCCA-1, candidate substance and cysteine protease, thereby suggesting remarkable suppression of the cysteine protease inhibitory activity of SCCA-1 by the candidate substance.

A substance screened according to the method described above is presumed to be a substance that has an inhibitory effect on the cysteine protease inhibitory activity of SCCA-1, and further has a high possibility of having a parakeratosis inhibitory function and being useful as a parakeratosis inhibitor.

Confirmation of the parakeratosis inhibitory function of such a substance can be easily carried out by applying to skin in which parakeratosis is occurring, such as the skin of a model animal, and then observing any healing effects. Thus, a screening method as claimed in the present invention is extremely useful as a method for primary screening of substances that inhibit parakeratosis among an infinite number of candidate substances such as herbal medicines. Examples of conditions in which parakeratosis is observed include skin diseases such as psoriasis, atopic dermatitis, porokeratosis, solar keratosis, seborrheic keratosis and lichen planus. Accordingly, a substance selected according to the screening method as claimed in the present invention is useful in the treatment and prevention of these skin diseases.

When the inventors of the present invention studied the inhibitory effects of various herbal medicines on the cysteine protease inhibitory activity of SCCA-1, it was found that cattail extract, grape extract, tomato extract, cucumber extract, kiwi extract and jujube extract possess such inhibitory effects. Thus, in a different aspect thereof, the present invention provides a skin composition for external use that inhibits epidermal parakeratosis by containing as an active ingredient thereof one or a plurality of types of herbal medicines selected from the group consisting of cattail extract, grape extract, tomato extract, cucumber extract, kiwi extract and jujube extract.

Extracts from these plants can be obtained by drying a plant raw material as necessary and then thinly slicing or crushing as necessary followed by extracting with an aqueous extraction agent or organic solvent. Examples of aqueous extraction agents that can be used include cold water, warm water or hot water at the temperature of the boiling point or lower, while examples of organic solvents that can be used include methanol, ethanol, 1,3-butanediol and ether, and these can be used either at normal temperature or after heating.

One type or two or more types of the aforementioned extracts can be randomly selected for use in the composition for external use as claimed in the present invention. The content of these extracts is preferably 0.001 to 20.0% by weight, more preferably 0.01 to 10.0% by weight, and particularly preferably 0.1 to 5.0% by weight, based on the total weight of the composition for external use. If the extract content is less than 0.001% by weight, there are cases in which the effects of the present invention may not be adequately demonstrated, while if the extract content exceeds 20.0% by weight, it may be difficult to formulate into a preparation, thereby making this undesirable.

The composition for external use of the present invention may be produced in accordance with ordinary methods, and although it can be produced with the aforementioned extracts alone, components ordinarily used in cosmetics, pharmaceuticals and other skin preparations for external use can be suitably incorporated as necessary in addition to the aforementioned extracts, examples of which include oils, surfactants, powders, colorants, water, moisturizers, thickeners, alcohols, various skin nutrients, antioxidants, ultraviolet absorbers, fragrances and antiseptics.

Other additives can also be suitably incorporated, examples of which include metal chelating agents such as disodium edetate, trisodium edetate, sodium citrate, sodium polyphosphate, sodium metaphosphate and gluconic acid, drugs such as caffeine, tannin, verapamil and derivatives thereof, licorice extract, glabridin, hot water extract of firethorn fruit, various herbal medicines, tocopherol acetate and glycyrrhizic acid and derivatives or salts thereof, whiteners such as vitamin C, magnesium ascorbyl phosphate, ascorbic acid glucoside, arbutin and kojic acid, sugars such as glucose, fructose, mannose, sucrose and trehalose, and vitamin A such as retinol, retinoic acid, retinyl acetate and retinyl palmitate.

A composition for external use of the present invention can be used as a cosmetic or over-the-counter medicine, and preferably as a cosmetic, applied to the outer skin, and can be used in a wide range of drug forms such as an aqueous liquid form, solubilized form, emulsified form, powder form, oily liquid form, gel form, ointment form, aerosol form, water-oil bilayer form or water-oil-water trilayer form. In addition, the composition for external use of the present invention can be applied to a wide range of drug forms such as foundation in the case of makeup cosmetics or as body soap or soap in the case of toiletry products. It can also be applied to a wide range of drug forms such as various types of ointments in the case of over-the-counter medicines. Those forms that can be adopted by the composition for external use of the present invention are not limited by these drug forms or product types.

In addition, the present invention provides a method for inhibiting epidermal parakeratosis by inhibiting the caspase-14 inhibitory activity of SCCA-1 in epidermal cells in order to normalize keratization of epidermal cells. Examples of conditions in which parakeratosis is observed include skin diseases such as psoriasis, atopic dermatitis, porokeratosis, solar keratosis, seborrheic keratosis and lichen planus as previously described. Although the present invention is preferably carried out by applying a skin composition for external use as claimed in the present invention to the skin, there are no particular limitations on the application method and dosage thereof, and are suitably determined according to the drug form of the skin composition for external use and the status of parakeratosis of the skin to be treated.

The following provides a more detailed explanation of the present invention through specific examples thereof. Furthermore, the present invention is not limited by these examples.

EXAMPLES (1) Method and Pharmaceutical Composition for Treatment of Psoriasis and/or Squamous Cell Carcinoma (1-i) Immunohistochemical Examination Biopsied epidermis was fixed with cold acetone and then embedded in paraffin in accordance with the AMeX procedure (Sato, Y., et al., Am. J. Pathol., 125, 431-435 (1986)). Thin sections were removed of paraffin with xylene and washed with acetone and then PBS. Next, non-specific binding sites of the thin sections were blocked with 10% normal rabbit serum (Histofine, Tokyo, Japan)

The epidermal thin sections were respectively incubated with anti-SCCA-1 monoclonal antibody (Santa Cruz Biotechnology, CA, USA) (diluted 1:500), anti-SCCA-2 monoclonal antibody (Santa Cruz Biotechnology, CA, USA) (diluted 1:500) or anti-SCCA polyclonal antibody (purified as described in Takeda, A., et al., J. Invest. Dermatol., 118, 147-154 (2002)). After washing with PBS, the thin sections were counter stained with hematoxylin and observed using the Dako Envision System (Dako Corp., CA, USA).

FIG. 1 shows the results of microscopic observations using epidermis specimens of epidermis from unexposed sites consisting of the upper arm (human, 24 years old), buttocks (human, 46 years old) and thigh (human, 75 years old) and epidermis from exposed sites consisting of the cheek (human, 20 years old, 76 years old) and eyelid (human, 82 years old), and using for the antibody anti-SCCA polyclonal antibody that binds with both SCCA-1 and SCCA-2. It can be understood from FIG. 1 that levels of SCCA are considerably higher in the upper layer of the epidermis of exposed sites as compared with unexposed sites. However, increased expression of SCCA was not observed in the basal layer even at exposed sites.

Figure 2:
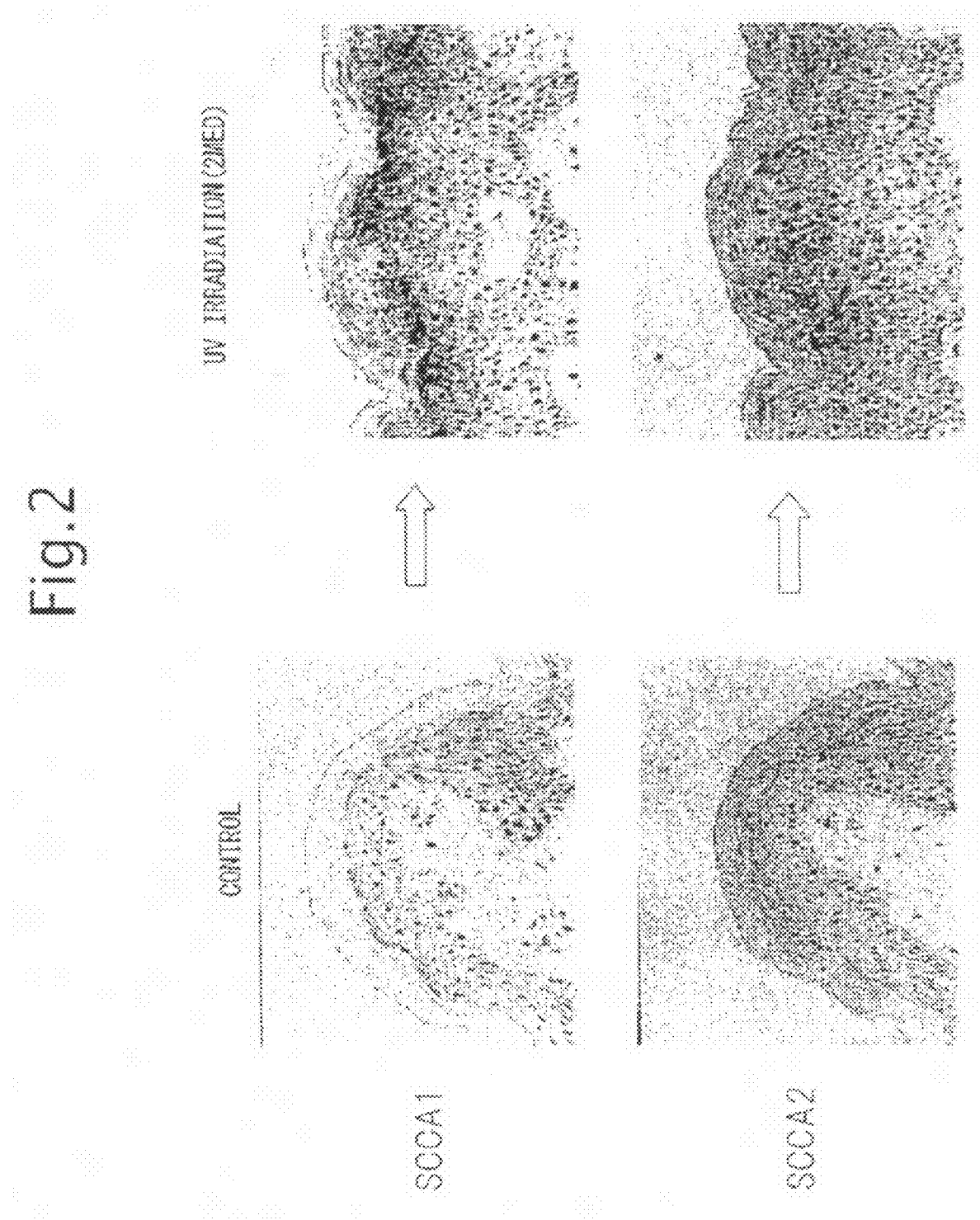
FIG. 2 shows fluctuations in expression of SCCA in epidermis due to UV irradiation.

FIG. 2 shows the results of microscopic observations of the expression of SCCA-1 and SCCA-2 in epidermis specimens consisting of human skin subjected to UV irradiation (Torex FL205-E-30/DMR Transluminator (Toshiba Medical Supply)) and control epidermis not subjected to UV irradiation, respectively. The antibodies used for both specimens consisted of anti-SCCA-1 monoclonal antibody and anti-SCCA-2 monoclonal antibody. It is clear from FIG. 2 that the expression of both SCCA-1 and SCCA-2 is increased as a result of irradiating human epidermis with UV light. In addition, this increased expression was prominent in the spinous layer and granular layer of the skin.

On the basis of these findings, it was clearly shown that expression of SCCA-1 and SCCA-2 is increased in the epidermis, and particularly in the spinous layer and granular layer, when the epidermis is irradiated with UV light.

(1-ii) Quantitative PCR Experiment

Next, an experiment was conducted to confirm that expression of SCCA-1 and SCCA-2 in the epidermis is increased by UV irradiation at the gene level.

Human keratinocytes were cultured in keratinocyte SFM medium (Gibco, Invitrogen) in the presence of L-glutamine and epithelial cell growth factor at 37° C. in a 5% $CO_2$ atmosphere with high humidity. Cells having a confluent density of 60 to 70% were irradiated with UVB for 0 to 48 hours. The cells were irradiated with UVB using the Torex FL205-E-30/DMR Transluminator (Toshiba Medical Supply) at an intensity of 50 $mJ/cm^2$. The control cells were not irradiated with UVB.

Total RNA from the cultured cells was isolated and purified using Isogen (Nippon Gene) in accordance with instructions provided. The expression levels of SCCA-1 and SCCA-2 were respectively determined by quantitative real-time polymerase chain reaction (PCR). Briefly speaking, total RNA was converted to cDNA using Superscript II (Invitrogen, Carlsbad, Calif.). That sample was then amplified by carrying out 40 cycles of 2-step PCR using the ABI PRISM 7900HT Sequence Detection System (Applied Biosystems, Foster City, Calif.). GAPDH (glyceraldehyde-3-phosphate dehydrogenase) was used for the internal standard.

The primers used were as described below.

```
SCCA-1:
Forward primer:
5'-GTGCTATCTGGAGTCCT-3'          (SEQ ID NO. 3)

Reverse primer:
5'-CTGTTGTTGCCAGCAA-3'           (SEQ ID NO. 4)

Taq Man probe:
5'-CATCACCTACTTCAACT-3'          (SEQ ID NO. 5)

SCCA-2:
Forward primer;
5'-CTCTGCTTCCTCTAGGAACACAG-3'    (SEQ ID NO. 6)

Reverse primer:
5'-TGTTGGCGATCTTCAGCTCA-3'       (SEQ ID NO. 7)

Taq Man probe:
5'-AGTTCCAGATCACATCGAGTT-3'      (SEQ ID NO. 8)

GAPDH:
Forward primer:
5'-GAAGGTGAAGGTCGGAGTC-3'        (SEQ ID NO. 9)

Reverse primer:
5'-GAAGATGGTGATGGGATTTC-3'       (SEQ ID NO. 10)

Taq Man probe:
5'-AGGCTGAGAACGGCAAGCTTGT-3'     (SEQ ID NO. 11)
```

A reporter dye (6-carboxyfluorescein) was coupled to the 5'-terminal of the Taq Man probe sequence, and a quencher dye (6-carboxytetramethylrhodamine) was incorporated on the 3'-terminal thereof.

Figure 3:
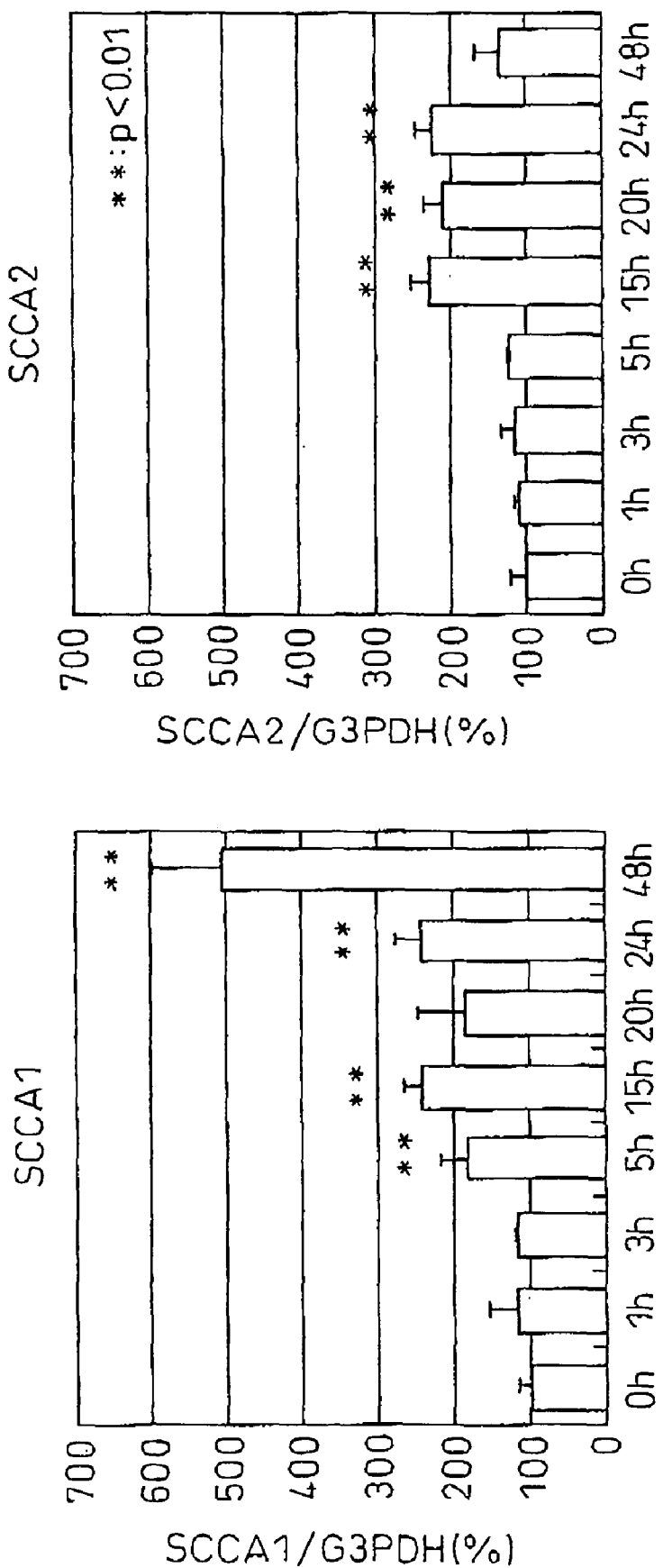
FIG. 3 shows the effects of UV irradiation on SCCA expression in cultured human keratinocytes.

FIG. 3 shows the results of the effects of UVB irradiation on the expression of SCCA in cultured human keratinocytes. Expression of SCCA-1 and SCCA-2 was clearly increased by UV irradiation. Thus, it is clear that expression of SCCA-1 and SCCA-2 is epidermal cells is increased at the gene level by UV irradiation.

Study of Role of SCCA in UV Irradiation

As has been described above, expression of SCCA-1 and SCCA-2 in epidermal cells is increased as a result of being subjected to UV irradiation. Next, a study was conducted as to the role played by SCCA-1 and SCCA-2 in epidermal cells subjected to UV irradiation.

(1-iii) Establishment of SCCA-1 and SCCA-2 Highly Expressing Cells

3T3 cells (acquired from ATCC) are cells derived from mouse fetuses that do not express SCCA-1 or SCCA-2. A gene encoding SCCA-1 or SCCA-2 was inserted into these cells as described below.

SCCA-1 and SCCA-2 cDNA (Takeda, A., et al., J. Invest. Dermatol., 118, 147-154 (2002)) was double-digested with BamHI and KpnI. These were then subcloned into a pTarget vector followed by insertion of 3T3 cells using Lipofectamine Plus (Gibco, Invitrogen). Briefly, 20 μg of cDNA in 675 μl of serum-free DMEM medium (Invitrogen Corp.), were mixed with 75 μl of Plus reagent and allowed to stand for 15 minutes at 25° C. Lipofectamine (100 μl) was added to 650 μl of serum-free DMEM medium followed by the addition thereof to the aforementioned cDNA-Plus mixture and allowing to stand for 15 minutes at 25° C. This cDNA mixture was then added to 10 ml of serum-free DMEM medium, and 3T3 cells were incubated therein for 4 hours at 37° C. in a 5% $CO_2$ atmosphere. The medium was replaced with DMEM medium containing 10% FCS (Invitrogen Corp.) and then incubated overnight. On the following day, G418 (Calbiochem) was added to a final concentration of 500 μg/ml. The G418 was maintained at this concentration throughout the culturing period. The medium was replaced every 2 to 3 days. After culturing for 4 weeks, several G418-resistant colonies were able to be isolated, and SCCA-1 and SCCA-2 expressing cell systems were established.

Cells inserted with cDNA encoding SCCA-1 (SCCA-1-inserted cells) were confirmed to specifically and stably express SCCA-1, while cells inserted with cDNA encoding SCCA-2 (SCCA-2-inserted cells) were confirmed to specifically and stably express SCCA-2. In addition, 3T3 cells inserted with a non-specific sequence using the same procedure (control cells) did not express SCCA-1 or SCCA-2.

A study was conducted on the roles played by SCCA-1 and SCCA-2 when epidermal cells were subjected to UV irradiation using the aforementioned SCCA-1-inserted cells, SCCA-2-inserted cells and control cells. More specifically, a study was made of the roles of SCCA-1 and SCCA-2 with respect to UV-induced apoptosis in epidermal cells.

Each of the aforementioned cells was cultured in DMEM medium containing 10% FCS at 37° C. in a 5% $CO_2$ atmosphere at high humidity. Cells' having a cluster density of 60 to 70% were irradiated with UVB for 0 to 48 hours. The cells were irradiated with UVB using the Torex FL205-E-30/DMR Transluminator (Toshiba Medical Supply) at an intensity of 50 $mJ/cm^2$.

Apoptosis was evaluated for these cells using the FACS Coulter (EPIX XL-MCL, Beckman Coulter), and analyzed by FACS (fluorescent activated cell sorting) using double staining with Annexin V-FITC and propidium iodine (PI) (Annexin V-FITC Kit, Immunotech) for the indicator.

Figure 4:
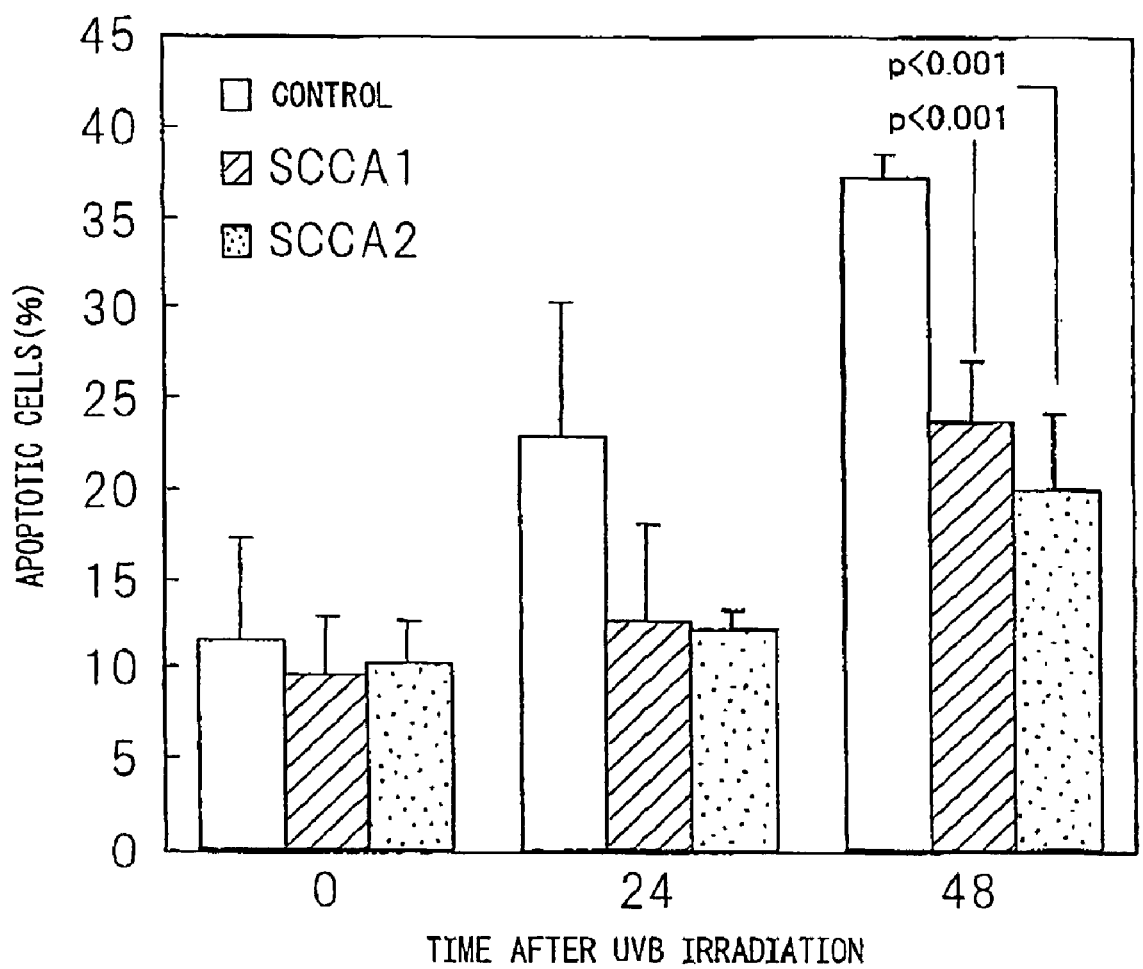
FIG. 4 shows a comparison of UV irradiation-induced apoptosis between SCCA highly expressing cells and SCCA non-expressing cells.

Those results are shown in FIG. 4. As is clear from FIG. 4, apoptosis attributable to UV irradiation was observed to decrease significantly for both the SCCA-1 and SCCA-2-inserted cells. Thus, SCCA-1 and SCCA-2 were presumed to be able to inhibit apoptosis induced by UV light.

In order to confirm this finding, the inventors of the present invention established SCCA-1 and SCCA-2 knockdown cell lines by RNA interference to further examine the roles of SCCA-1 and SCCA-2 in epidermal cells subjected to UV irradiation.

(1-iv) Establishment of SCCA Knockdown Cells

HaCat cells (H. Hans, et al., Experimental Cell Research, 239, 399-410 (1998)) are human keratinocytes that highly express SCCA. SCCA-1 and SCCA-2 knockdown cell lines were established by constitutively expressing siRNA (short interference RNA) with a pSilencer vector (Ambion) in accordance with the procedure for RNA interference.

The siRNA was constructed using pSilencer vector according to the instructions provided. More specifically, a double-stranded oligonucleotide consisting of a 65 mer sense oligonucleotide (SEQ ID NO. 12) containing a 21 mer oligonucleotide (ACATGAACTT GGTGTTGGCT T: SEQ ID NO. 1) complementary to nucleotides at positions 46 to 66 of a gene encoding SCCA, and a 65 mer antisense oligonucleotide (SEQ ID NO. 13) containing a 21 mer oligonucleotide (AAGCCAACAC CAAGTTCATG T: SEQ ID NO. 2) homologous with nucleotides at positions 46 to 66, was cloned to the HindIII site and BamHI site of pSilencer vector. Transfection to HaCat cells was carried out using Lipofectamine 2000 (Invitrogen) in accordance with the instructions provided. Control cells were prepared by using a double-stranded oligonucleotide consisting of two oligonucleotides neither significantly homologous or complementary to mammalian gene sequences. A stable cell system was acquired by selecting transfected cells in hygromycin B selective medium after culturing for 4 to 6 weeks. The procedure described above was used to confirm whether expression of SCCA was inhibited, and expression of SCCA-1 and SCCA-2 was measured by real-time PCR.

Sense oligonucleotide
(SEQ ID NO. 12)
GATCCCGGCCAACACCAAGTTCATGTTTCAAGAGA ACATGAACTTGGTG

TTGGCTTTTTTGGAAA (underline indicates homologous region)

Antisense oligonucleotide
(SEQ ID NO. 13)
AGCTTTTCCAAAA AAGCCAACACCAAGTTCATGTTCTCTTGAAACATGA

ACTTGGTGTTGGCCGG (underline indicates complementary region)

Figure 5:
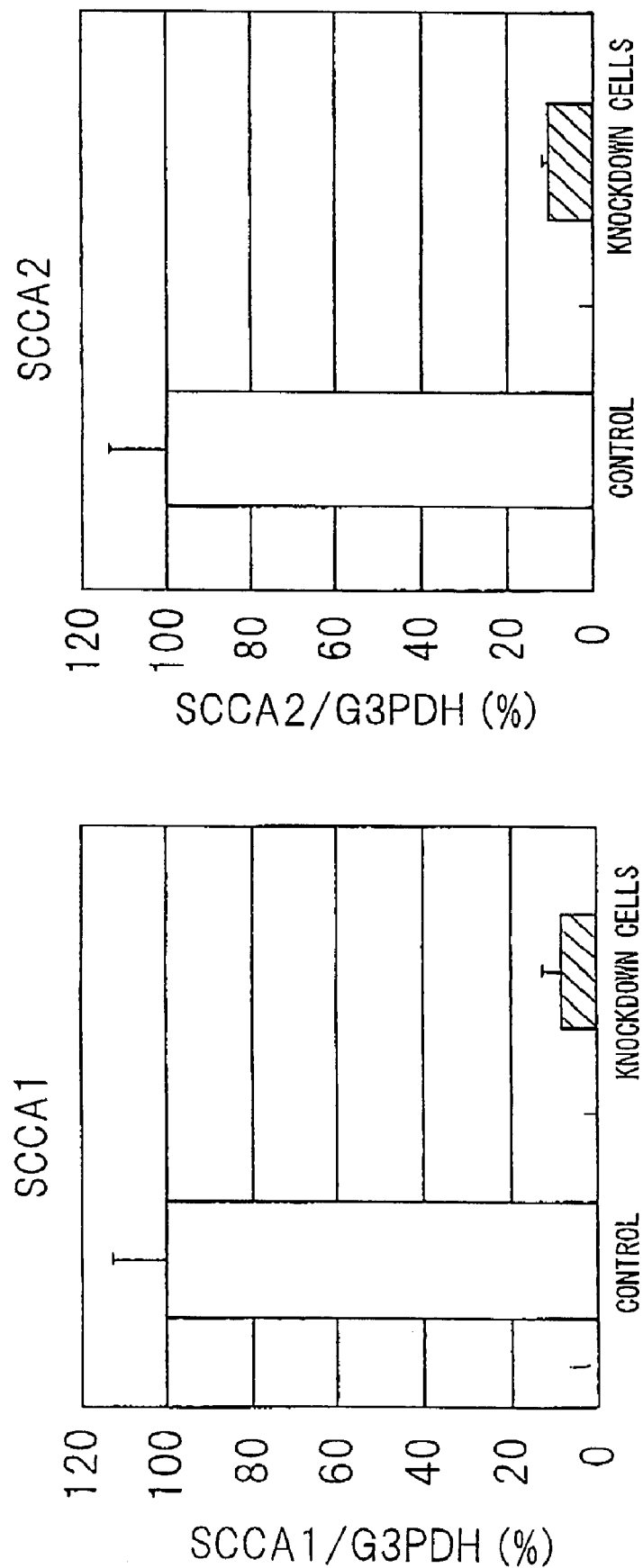
FIG. 5 shows the establishment of an SSCA knockdown cell line.

Those results are shown in FIG. 5. Expression of SCCA-1 and SCCA-2 was confirmed to be inhibited (knocked down) by 90% or more in cells inserted with siRNA as described above in comparison with the control cells.

A study was then made on the roles of SCCA-1 and SCCA-2 with respect to UV-induced apoptosis in epidermal cells using these knockdown cells and control cells.

Each of the cells was cultured in keratinocyte SFM medium (Gibco, Invitrogen) in the presence of L-glutamine and epithelial cell growth factor at 37° C. in a 5% $CO_2$ atmosphere with high humidity. Cells having a confluent density of 60 to 70% were irradiated with UVB. The cells were irradiated with UVB using the Torex FL205-E-30/DMR Transluminator (Toshiba Medical Supply) at an intensity of 50 mJ/cm².

Apoptosis was evaluated for these cells using the FACS Coulter, and analyzed by FACS (fluorescent activated cell sorting) using double staining with Annexin V-FITC and propidium iodine (PI) (Annexin V-FITC Kit, Immunotech) for the indicator.

Figure 6:
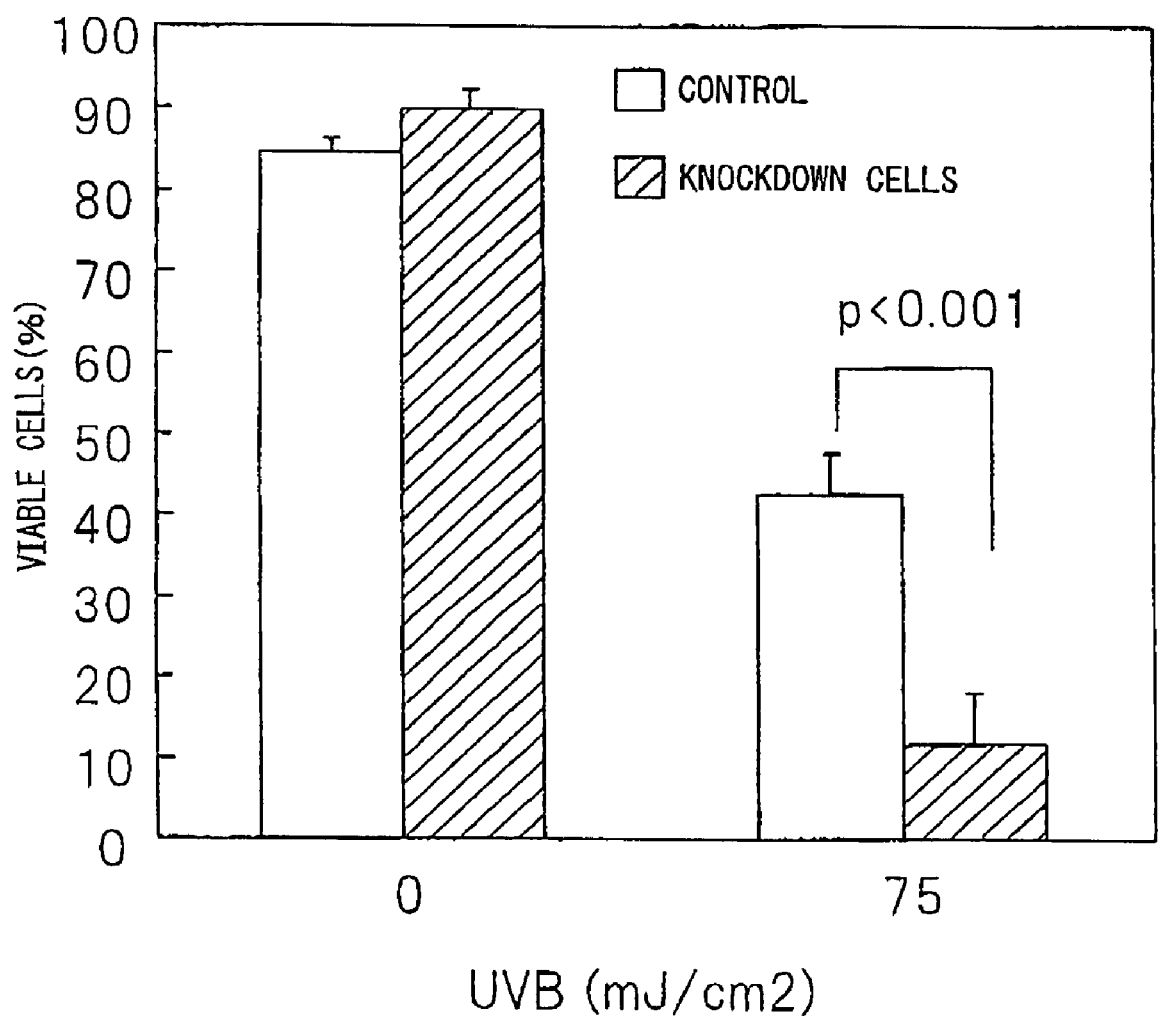
FIG. 6 shows a comparison of rates of apoptosis induced by UV irradiation between SCCA knockdown cells and control cells.

Those results are shown in FIG. 6. As a result of irradiating knockdown cells with UV light, in contrast to apoptosis occurring in 38% of the control cells, apoptosis was induced in roughly 80% of the knockdown cells. Thus, SCCA was determined to significant inhibit apoptosis of epidermal cells induced by UV irradiation. Accordingly, SCCA was clearly determined to be responsible for the UV defense mechanism of epidermal cells, while also being a protein having an action that inhibits apoptosis.

(2) Method for Screening for Substances Inhibiting Parakeratosis, Substances Screened by this Method and Method for Inhibiting Parakeratosis (2-i) Materials and Methods Materials Ac-WEHD-MCA, Ac-YVAD-MCA, Ac-VDVAD-MCA, Ac-DEVD-MCA, Ac-VEID-MCA, Ac-IETD-MCA and Ac-LEHD-MCA were purchased from Peptide Institute, Inc. (Osaka, Japan).

Benzyloxycarbonyl (Z)-YVAD-FMK, Z-VDVSD-FMK, Z-DEVD-FMK, Z-VEID-FMK, Z-IETD-FMK, Z-LEHD-FMK and Z-VAD-FMK were purchased from BioVision (Mountain View, Calif.). Recombinant caspases-1 to 10 were obtained from BIOMOL Research Labs, Inc. (Plymouth Meeting, Pa.).

H-99 antibody (Santa Cruz Biotechnology, Inc.) was used to detect the pro-forms and large subunits of caspase-14. H-99 antibody is an antibody that occurs in response to peptides corresponding to amino acids 24 to 122 of human caspase-14, and therefore reacts with proenzymes of caspase-14 and their processed forms, namely their large subunits.

C-20 antibody (Santa Cruz Biotechnology) was used to detect small subunits of caspase-14. Cleavage site-specific antibody (h14D[146]) was prepared immunizing a rabbit with a synthetic pentapeptide TVGGD equivalent to the presumed processing site of human caspase-14.

(2-ii) Measurement of WEHD-MCA Hydrolysis Activity

Caspase-14 activity was measured using Ac-WEHD-MCA as substrate by adding some degree of variation to the method described in Mikolajczyk, J. et al., Biochemistry, 43, 10560-9 (2004). Briefly, the assay mixture was prepared from 45 µl of 0.1 M HEPES buffer (pH 7.5), 0.06 M NaCl, 0.01% CHAPS, 5 mM DTT, 1.3 M sodium citrate and 10 µM WEHD-MCA (all concentrations indicate the final concentrations). An enzyme sample (5 µl) was added to this mixture followed by incubating for 10 to 30 minutes. The reaction was stopped with 150 µl of 0.1 M monochloroacetic acid, and measurements were performed at an excitation wavelength of 355 nm and emission wavelength of 460 nm using Fluoroskan Ascent FL (Thermo Electron Co., Wolsam, Mass.) In the case of the inhibitor assay, caspase-14 and peptide inhibitor were incubated in the assay buffer for 15 minutes, and the assay was started with the addition of 5 µl of 100 µM WEHD-MCA.

(2-iii) Purification of Caspase-14

Human cornified cells (approx. 14 g) scraped from the heels of healthy individuals were extracted with 0.1 M Tris-HCl (pH 8.0) containing 0.14 M NaCl using a glass homogenizer. A supernatant was obtained after centrifuging at 15,000 g for 60 minutes. After concentrating with Amicon Ultra (Millipore, Mass.) and desalting with the Fast Desalting Column HR10/10 (Amersham Biosciences), the crude product was applied to a HiPrep 16/10 QXL column. The column was washed with 20 mM Tris-HCl (pH 8.0) and eluted at a linear NaCl gradient of 0 to 1 M. The fractions were traced by Western blotting using anti-caspase-14 antibody (H-99) (Santa Cruz Biotechnology, CA) and h14D[146] antibody. In addition, hydrolysis activity with respect to Ac-Tyr-Glu-His-Asp-methyl-coumarin amide (WEHD-MCA) (Peptide Institute, Inc., Osaka, Japan) was measured for each fraction. Positive fractions were placed on a Mono Q column equilibrated with the same buffer and eluted a maximum NaCl gradient of 1 M. The caspase-14 fraction was further separated by Mono S cationic exchange chromatography. The column was equilibrated with 20 mM acetate buffer (pH 4.5) and eluted at an NaCl gradient of 0 to 1 M. Positive fractions were concentrated and placed on a chromatofocusing Mono P column equilibrated with 25 mM ethanolamine (pH 8.3). The column was eluted while forming a pH gradient from 8 to 5 using 46 ml of Polybuffer (pH 5.0). The caspase-14 was finally purified using Superdex 75 gel chromatography. The protein concentration was determined with the BioRad Protein Assay Kit (BioRad Lab, Hercules, Calif.).

(2-iv) Preparation of Recombinant Caspase-14 and SCCA-1 cDNA encoding caspase-14 was isolated and amplified from keratinocyte cDNA by PCR using a forward primer in the form of AAGGATCCAATCCGCGGTCTTTGGAA-GAGGAG (SEQ ID NO. 14) and a reverse primer in the form of (SEQ ID NO. 15)
TTTCTGCAGGTTGCAGATACAGCCGTTTCCGGAGGGTGC.

The PCR product was cloned in a pQE-100 DoubleTag vector (Qiagen, Valencia, Calif.) and expressed in E. coli JM109.

SSCA1 cDNA was separated from a cDNA library (Takeda, A., et al., J. Invest. Dermatol., 118, 147-154 (2002)) and cloned in pQE30 vector (Qiagen). Recombinant protein was purified with Ni-NTA Agarose (Qiagen) and Mono Q chromatography.

(2-v) Immunohistochemistry

Human scalp samples were obtained by plastic surgery after acquiring patient consent. The tissue was fixed with 4% paraformaldehyde (PFA) in phosphate buffer solution (pH 7.4) and then embedded in paraffin. Thin sections were then prepared followed by incubation with suitable antibody overnight at 4° C. Peroxidase-coupled goat anti-rabbit IgG (Nichirei Corp.) was used as secondary antibody and reacted with a color developing reagent in the form of DAB.

In the case of double staining detection of TUNEL-positive cells and active caspase, Texas Red (registered trademark) dye-coupled anti-rabbit IgG (Rova) was used as secondary antibody. The TUNEL reaction was carried out using a fluorescein in situ cell death detection kit (Roche Diagnostics) in accordance with the instructions provided by the manufacturer.

Antibodies ICAD IgG (FL331, Santa Cruz Biotechnology) and DFF45/ICAD Ab-2 (NeoMarkers, Fremont, Calif.) were used in the case of ICAD Western blotting and immunohistochemical analysis.

Clustered parakeratosis has been reported to be frequently observed in the skin of active atopic dermatitis (AD) patients (Sakurai, K., et al., J. Dermatol. Sci., 30, 37-42 (2002); Piloto Valdes, L., et al., Allergol. Immunopathol. (Madr), 18, 321-4 (1990)). In this experiment, the localization of ICAD and SCCA-1 in parakeratotic skin was investigated using a non-invasive method. A sample of the superficial cornified layer was collected from the skin of an AD patient and healthy volunteer, and adhered to slide glasses using the medical adhesive, Aron Alpha A (Sankyo Co., Tokyo). After fixing with 3% formaldehyde, the samples were permeated with 0.1% Triton X-100 followed by immunostaining with anti-ICAD or anti-SCCA-1 antibody overnight at 4° C. Alexa Fluor 400-coupled anti-rabbit antibody (ICAD) or anti-mouse IgG (SCCA-1) antibody were respectively used as secondary antibody at room temperature for 1 hour. The samples were immersed for 5 minutes in 0.1% pyridium iodide to visualize the nuclei and then washed three times with PBS. The Leica DMLA microscope was used for fluorescent microscopy.

(2-vi) Western Blot Analysis

Protein was separated by SDS-polyacrylamide gel electrophoresis at a concentration gradient of 5 to 20%. Following electrophoresis, the protein was transferred to a polyvinylidene difluoride membrane (Immobilon-P, Millipore, Bedford, Mass.) and then incubated with anti-caspase-14 antibody containing H-99, h14D$^{146}$ or C20. Immunoreactive protein was visualized by chemiluminescence with the ECL-Plus (Amersham) using peroxidase-labeled anti-rabbit IgG (Sigma) or anti-goat IgG as secondary antibody.

(2-vii) Results

Keratinocyte Caspase-14 Processed with Asp$^{146}$

Figure 8:
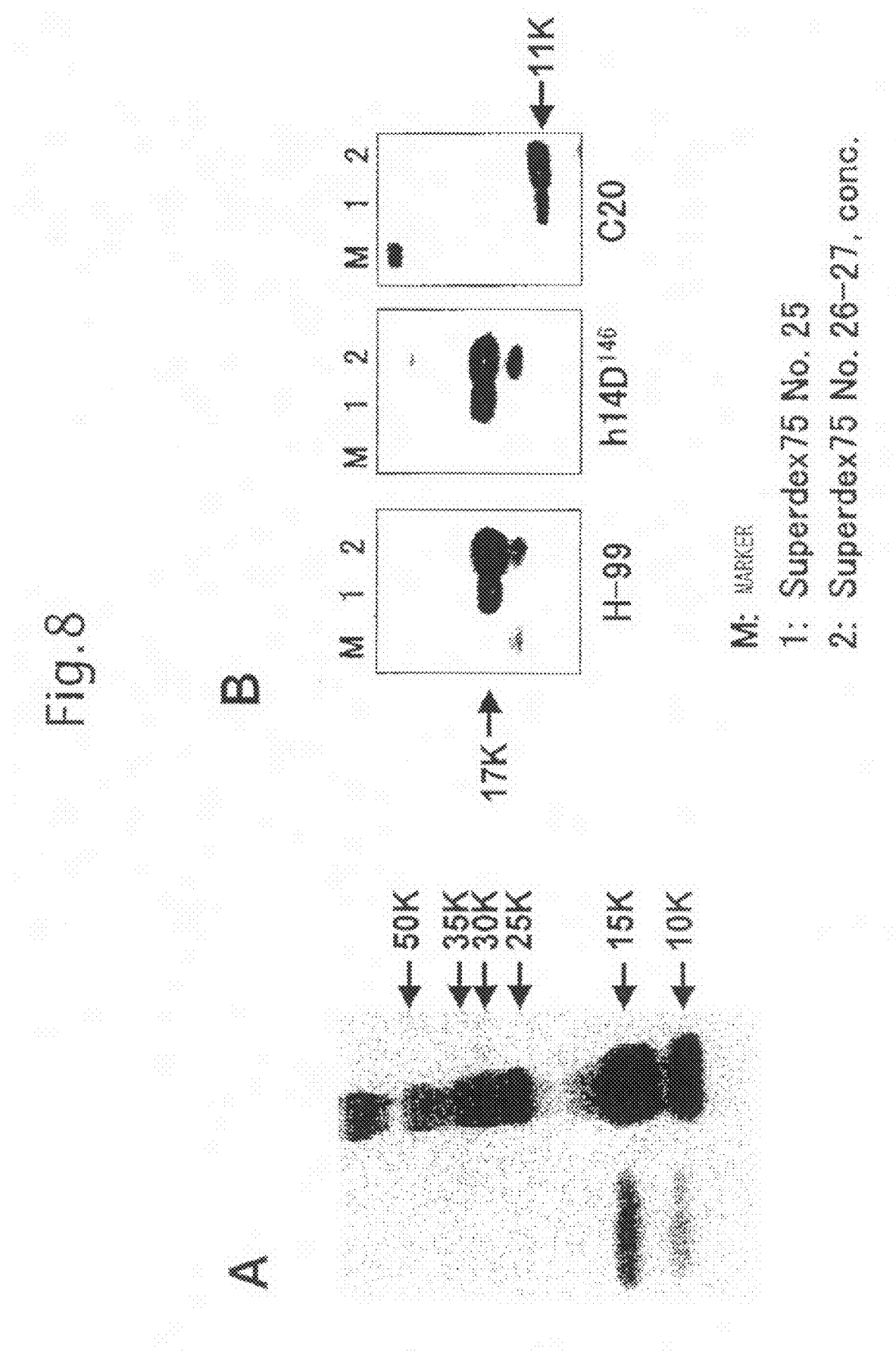
FIG. 8 shows an analysis of purified caspase-14. (A) Fraction No. 25 obtained from Superdex 75 chromatography following SDS polyacrylamide gel electrophoresis was transferred to a PVDF membrane and stained with Coomassie brilliant blue. Two protein bands were observed at 17 KDa and 11 KDa. (B) Western blot analysis using H-99, h14D$^{146}$ and C20 antibodies. The 17 KDa band was observed to be positive for both the H99 and h14D$^{146}$ antibodies, while the 11 KDa band was recognized with C20 antibody.

According to Western blot analysis, only a 17 KDa band was detected in keratinocyte extract for H-99 antibody (FIG. 8). This result does not agree with the result for extracts derived from whole skin or skin-equivalent models containing an unprocessed 30 KDa form. This 17 KDa band was also recognized with h14D$^{146}$ antibody (FIG. 8B), and is presumed to be a large subunit of active caspase-14 (p17). This suggests that maturation of caspase-14 is achieved by cleavage at Asp$^{146}$ during the final stage of terminal differentiation. Moreover, the 30 KDa band was also recognized by H-99 and h14D$^{146}$ antibody in a skin-equivalent model, suggesting cleavage at Asp$^{146}$.

(2-viii) Preparation of Caspase-14 from Keratinocyte Extract

The majority of the caspase-14 in keratinized cells is in a processed form, and for this reason, since it presumed to be present in an active form (Eckhart, L., et al., J. Invest. Dermatol., 115, 1148-51 (2000); Lippens, S., et al., Cell Death Differ., 7, 1218-24 (2000); Mikolajczyk, J., et al., Biochemistry, 43, 10560-9 (2004)), human keratinocytes are thought to be a superior source of purified caspase-14. However, human keratinocytes are also known to contain caspase-1-like enzyme (Takahashi, T., et al., Invest. Dermatol., 111, 367-72 (1998)). Substrates of caspase-1 such as WEHD-substrate can be hydrolyzed by both caspase-1 and caspase-14. The inventors of the present invention first tested hydrolysis of WEHD-MCA by caspase-1 with 1.3 M sodium citrate and in the presence and absence of 5 mM dithiothreitol. Despite WEHD-MCA being a superior substrate of caspase-1 in standard caspase assay buffer, caspase-1 was confirmed to be unable to hydrolyze this substrate in the presence of kosmotropic ion (data not shown). Thus, each fraction was evaluated by three methods consisting of hydrolysis activity on WEHD-MCA, reactivity with H-99 and h14D$^{146}$ antibody. Table 1 shows the results of continuous chromatography. Following the initial anionic exchange chromatography using a HiPrep Q column, the yield demonstrated an increase of 170%, while specific activity increased roughly ten-fold. This increase was probably attributable to the dissociation of caspase-14 from an intrinsic inhibitor. According to Western blot analysis, fractions nos. 16 to 20 were shown to contain 17 KDa bands positive for H-99 and h14D$^{146}$. These fractions were also observed to demonstrate WEHD-MCA hydrolysis activity. In the subsequent Mono Q anionic exchange chromatography, fractions Nos. 25 to 29 contained a processed form of caspase-14 in accordance with an assessment made based on the presence of 17 KDa bands positive for H-99 and h14D$^{146}$. Only these fractions were observed to demonstrate WEHD-MCA hydrolysis activity, Mono S cationic chromatography and Mono P chromatofocusing were effective for removing the major contaminant proteins, and specific activity increased 3.5-fold and 7-fold, respectively. Here again, only the H-99 and h14D$^{146}$-positive fractions demonstrated WEHD-MCA hydrolysis activity. In the final stage using Superdex 75 chromatography, a peak having a molecular weight of 30 KDa was separated, and this peak coincided with the peak for WEHD-MCA hydrolysis activity. In SDS-polyacrylamide gel electrophoresis, this preparation was shown to contain 17 KDa and 11 KDa fragments. The former was positive for both H-99 antibody and h14D$^{146}$ antibody, while the latter was recognized with C20 antibody. This suggests that human caspase-14 is purified in the form of a heterodimer composed of a large subunit (17 KDa) and a small subunit (11 KDa). In addition, Superdex 75 chromatography indicated that, differing from other caspases, caspase-14 in human keratinocytes is present in the form of a monomer in the manner of a granzyme B-activated form. Table 1 provides a summary of the purification rates of caspase-14. 11.8 μg of purified protein were obtained starting from about 100 mg of soluble protein extract. Specific activity increased 764-fold and the yield was 9.1%.

TABLE 1

Summary of Purification of Caspase-14

| | Protein concentration μg/ml | Volume ml | Total protein weight μg | Enzyme activity AFU (mU) | Specific activity (mU/mg protein) | Total activity U | Yield (%) |
| --- | --- | --- | --- | --- | --- | --- | --- |
| CC TBS Ext. | 312.0 | 320.00 | 99840.0 | 3.67 | 11.8 | 587.34 | 100.0 |
| HiPrep Q | 1185.0 | 15.00 | 17775.0 | 133.59 | 112.7 | 1001.92 | 170.6 |
| Mono Q | 582.0 | 8.00 | 4656.0 | 150.30 | 258.2 | 601.19 | 102.4 |

TABLE 1-continued

Summary of Purification of Caspase-14

| | Protein concentration μg/ml | Volume ml | Total protein weight μg | Enzyme activity AFU (mU) | Specific activity (mU/mg protein) | Total activity U | Yield (%) |
|---|---|---|---|---|---|---|---|
| Mono S | 61.3 | 8.00 | 490.4 | 56.94 | 928.8 | 227.75 | 38.8 |
| Mono P | 50.5 | 1.00 | 50.5 | 338.31 | 6699.2 | 169.15 | 28.8 |
| Superdex 75 | 11.8 | 1.00 | 11.8 | 106.52 | 9015.1 | 53.26 | 9.1 |

(2-viv) Enzyme Characteristics of Purified Caspase-14

Figure 9:
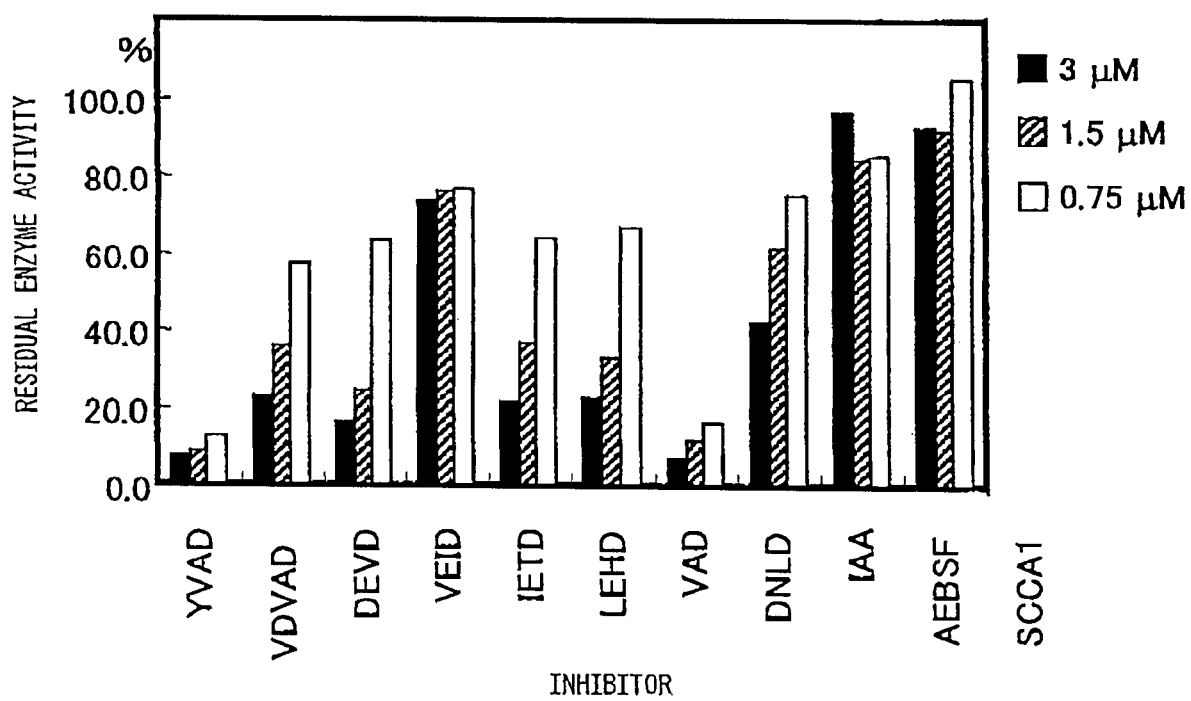
FIG. 9 shows the results of various inhibitors on purified caspase-14. Caspase-14 was incubated with peptide inhibitors of caspase (consisting of YVAD, VDVAD, DEVD, VEID, IETD, LEHD and DNLD) and class-specific inhibitors of cysteine proteinase (IAA) and serine proteinase (AEBSF). Residual enzyme activity was measured using WEHD-MCA as substrate in the presence of 1.3 M sodium citrate and 5 mM DTT. The enzymes were tested at concentrations of 5, 2.5 and 1.25 μM, respectively. The values are shown as the average values of duplicate assays.

The enzyme characteristics of purified caspase-14 were investigated (FIGS. 9 and 10). Caspase-14 had sensitivity to various caspase inhibitors such as YVAD-FMK (caspase-1 inhibitor), VDVAD-FMK (caspase-2 inhibitor), DEVD-FMK (caspase-3 inhibitor), IETD-FMK (caspase-8 inhibitor), LEHD-FMK (caspase-9 inhibitor) and VAD-FMK (pan-caspase inhibitor) (FIG. 9). Furthermore, VEID-FMK had hardly any effect. YVAD-FMK in particular demonstrated extremely potent inhibitory effects on caspase-14 activity. This is probably due to the structural similarity between caspase-1 and caspase-14. The pan-caspase inhibitor, VAD-FMK, inhibited caspase activity to about the same degree as VAD-FMK. The cysteine protease class-specific inhibitor, iodoacetic acid (IAA), or serine protease class-specific inhibitor, 4-(2-aminoethyl)benzenesulfonyl fluoride (ABBSF), did not exhibit significant inhibitory effects at the test concentrations used in this study.

(2-x) Effects of Purified Caspase-14 on ICAD Decomposition

The inventors of the present invention tested the effects of caspase-14 on ICAD during the course of searching for natural substrates of caspase-14. This is because disappearance of the nucleus is an extremely important event for terminal differentiation. According to an assessment made by Western blot analysis using anti-ICAD IgG when recombinant ICAD protein and purified caspase-14 were incubated in an ordinary caspase assay buffer, purified caspase-14 did not demonstrate any hydrolysis activity on ICAD (FIG. 10A). However, since the amount of intact ICAD protein decreases and two major decomposition products increase in the presence of kosmotropic salt, purified caspase-14 demonstrated limited decomposing action on ICAD.

(2-xi) Inhibition of Caspase-14 by SCCA-1

Although SCCA-1 is a member of the serpin superfamily, it inhibits cysteine proteases such as papain and cathepsin L (Takeda, A., et al., Biol. Chem., 383, 1231-6 (2002)). This indicates that SCCA-1 is a unique class inhibitor in the manner of Crm-A[32]. Thus, the inventors of the present invention conducted a test as to whether or not SCCA-1 is able to inhibit caspase members. Kosmotropic conditions were used in the case of caspase-14. None of the caspase members (1 to 10) were affected with respect to enzyme activity when recombinant caspase was incubated with SCCA-1 (FIG. 10C). SCCA-1 inhibited decomposition of ICAD by caspase-14. Recovery of enzyme activity was not observed even if the incubation time increased. This suggests that strong binding between caspase-14 and SCCA-1 (FIG. 10B).

(2-xii) Localization of Active Caspase-14 and TUNEL-Positive Cells

Figure 11:
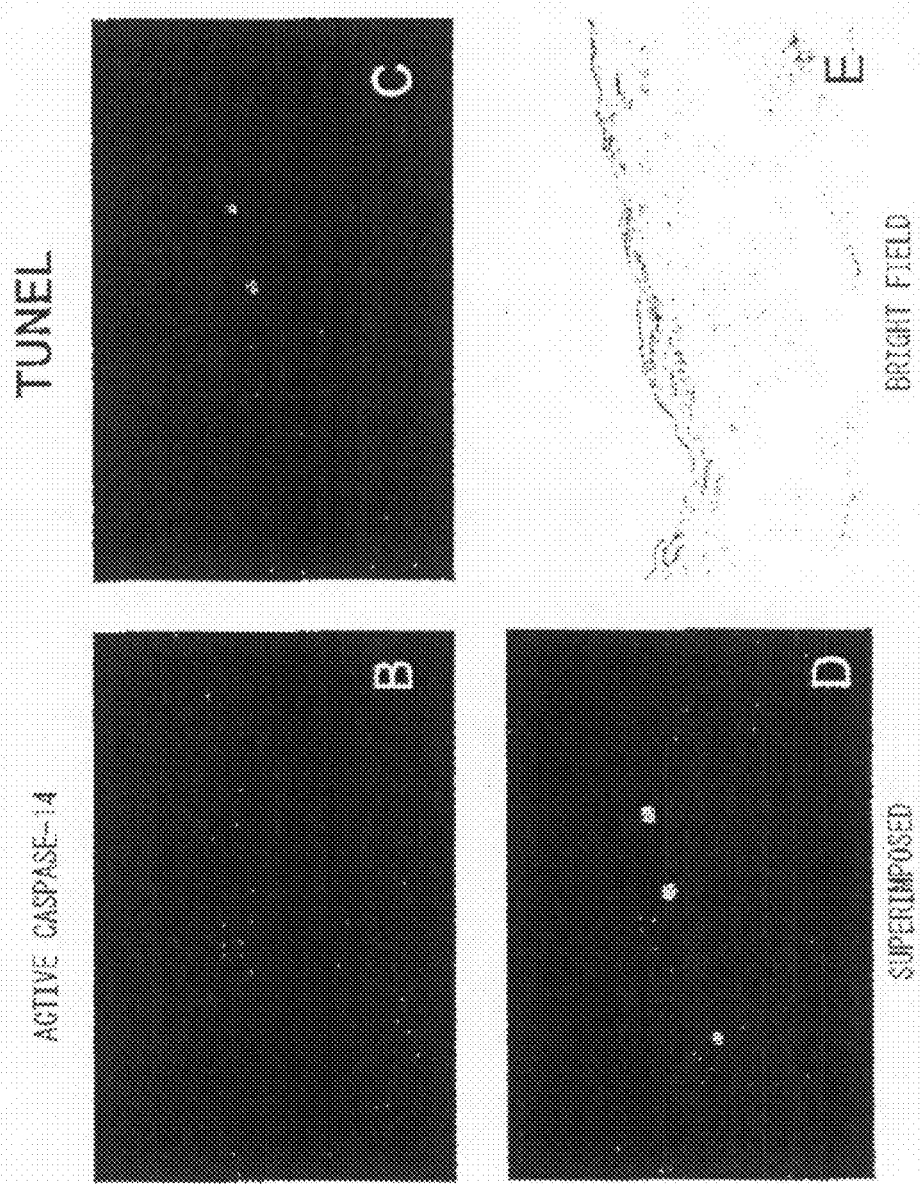
FIG. 11 shows the localization of active caspase-14 and TUNEL-positive cells. Thin sections of normal human skin were stained with H-99 antibody (A), h14D$^{146}$ antibody (B) and TUNEL (C). Texas-Red was used for fluorescent detection (B). FITC was used for the TUNEL, Texas-Red was used for immunostaining, and double staining was performed for TUNEL and caspase-14.

In order to investigate whether caspase-14 is involved in the denucleation process, the inventors of the present invention carried out caspase-14 and TUNEL double staining. As shown in FIG. 11A, caspase-14 containing pro-forms and active forms was localized in cells ranging from prickle cells to keratinocytes in normal human epidermis. This agrees with previous findings (Lippens, et al. (2000), op cit). Active caspase-14 detected with h14D[146] antibody was limited to some keratinocytes and granular cells (FIG. 11B). Nearly all keratinocytes were unevenly stained. Although TUNEL-positive cells were observed immediately beneath the cornified layer, the localization of the majority of these positive cells was extremely limited (FIG. 1C). It is interesting to note that TUNEL-positive cells were nearly always localized with h14D[146]-positive cells. This suggests that DNA fragmentation is occurring in these cells, and that active caspase-14 is involved in this process.

(2-xiii) Co-localization of ICAD and SCCA-1 in Parakeratotic Nuclei

Figure 12:
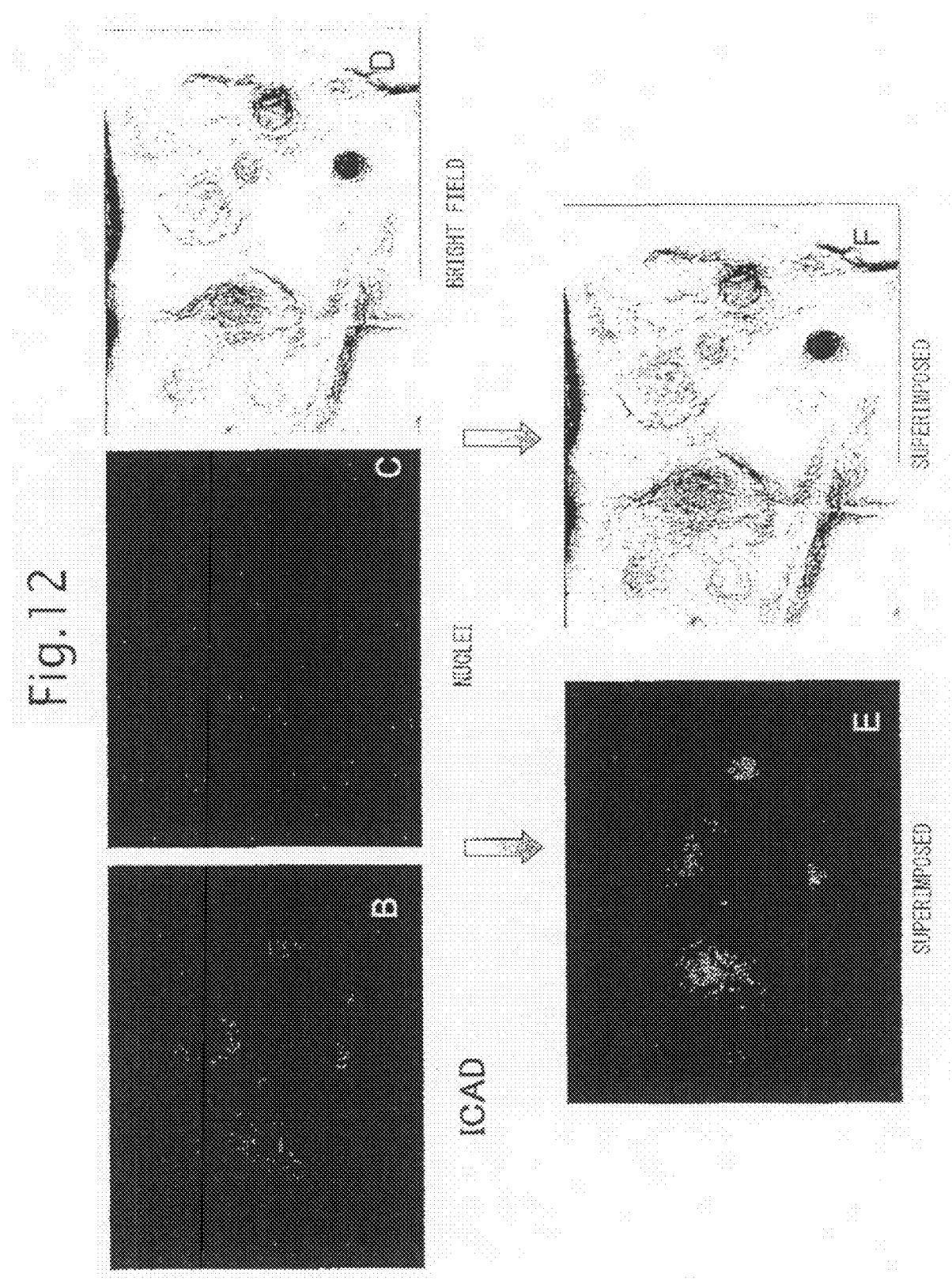
FIG. 12 shows the co-localization of ICAD and parakeratotic nuclei. Thin sections of normal human skin were stained with anti-ICAD antibody FL331. Nearly all subepidermal nuclei were positive for this antibody. When ICAD on the superficial layer of keratinocytes from the skin of AD patients was stained with antibody, positive sites of various sizes were observed (B). Nuclear staining with propidium iodide (PI) showing nuclear clusters was frequently observed (C). Bright field observations of the same sites-indicated overlapping scales on the surface (D). Superimposed images clearly demonstrated the presence of ICAD only at sites of parakeratosis (E). Superimposed images of nuclear staining were also indicated in bright field observations (F).

The use of FL331 antibody reveals that ICAD is primarily localized in the nuclei of basal cells and basal epithelial cells in longitudinal cross-sections of normal human skin. The cytoplasm was weakly positive in cells ranging from basal cells to granular cells. In the cornified layer, immunoreactivity to ICAD decreased considerably. Substantially the same results were obtained even when using the N-terminal peptide antibody, DFF45/ICAD Ab-2 (data not shown). In the case of staining the superficial cornified layer of AD patients with anti-ICAD antibody (FL-331), various sizes of cluster regions were positive for this antibody (FIG. 12B). Nuclear staining by PI indicated that parakeratotic nuclei are consistently found in these porphyritic islands (FIG. 12C). Bright field observations of the superficial cornified layer revealed a coarse surface with numerous surface irregularities (FIG. 12D). Superimposed images indicated that parakeratotic sites coincided with ICAD-positive sites (FIGS. 12E and 12F). These results suggest that decomposition of ICAD is required for elimination of nuclei during terminal differentiation.

Extremely low levels of SCCA-1 were detected in the granular layer in the case of normal human skin. Strong immunostaining with a prominent porphyritic distribution of positive sites was observed in the superficial cornified layer of active AD as well. (FIG. 13A). Similarly, SCCA-1-positive regions coincided with the PI-positive nucleus layer, namely parakeratotic sites (FIGS. 13J to 13L). In summary, these results suggest that the ICAD/CAD system plays an important role in the denucleation process, and that SCCA-1 is involved in this reaction as a suppressor.

DISCUSSION

The majority of caspase-14 is expressed in the epidermis, while hardly being expressed at all in other tissues (Van de Craen, M., et al., Cell Death Differ., 5, 836-46 (1998)). According to previous reports, terminal differentiation of keratinocytes is linked with the processing of caspase-14, and this suggests the activation of caspase family proteinases (Lippens, S. et al., Cell Death Differ., 7, 1218-24 (2000); Eckhart, L., Biochem. Biophys. Res. Commun., 277, 655-9 (2000); Hu, S., J. Biol. Chem., 273, 29648-53 (1988)). More recently, Mikolajaczyk et al. (2004, op cit) demonstrated that granzyme B-cleaving caspase-14 is enzymatically active in the presence of kosmotropic salt. In this study, the inventors of the present invention attempted to purify caspase-14 from completely differentiated keratinocytes to investigate whether or not human caspase-14 is active at the final stage of keratinocyte differentiation. The inventors of the present invention used three types of antibodies that recognize a large subunit, pro-form (H-99, having a presumed caspase cleaving site at $Asp^{146}$ ($h14D^{146}$)) and small subunit (C20), respectively. The final preparation was composed of two bands, namely a 17 KDa band recognized by $h14D^{146}$ antibody, and an 11 KDa band recognized by C20 antibody. These protein bands are the large and small subunits of active caspase-14. During the purification process, an H99-positive 17 KDa band was recognized together with $h14D^{146}$ antibody. This suggests that the carboxyl terminal of the large subunit ends with $Asp^{146}$. The amino terminal region of the small subunit was identified as $Lys^{153}$-Asp-Ser-Pro-Gln, and this suggests that processing occurs between $Ile^{152}$ and $Lys^{153}$. This site is a specific cleaving site for members of the caspase family. This agrees with the finding of Chien, et al. (Biochem. Biophys. Res. Comaun., 2002, Aug. 30: 296(4): 911-7) that caspase-14 immunoprecipitated from foreskin extract demonstrates cleavage at the same site. Thus, it was concluded that human caspase-14 is homogeneously purified in the form of a highly active beterodimer. Processing at the two sites of $Asp^{146}$ and $Ile^{152}$ and removal of six residues within linker regions $Xxx^{147}$ and $Ile^{152}$ were suggested to be involved in the maturation of caspase-14. The presence of two different cleavage sites (one being acidic and the other being hydrophobic) also suggests that activation of caspase-14 is carried out in multiple steps by numerous enzymes.

The enzymatic characteristics of purified caspase-14 were extremely unique. Purified caspase-14 exhibited a comparatively broad range of inhibitor sensitivity to known caspase inhibitors. In particular, the caspase-1 inhibitor, YVAD-FMK, exhibited the most potent inhibitory action. YVAD-FMK also demonstrated higher activity than WEHD-MCA and another caspase-1 substrate in the form of YCAD-MCA. This suggests that caspase-1 and caspase-14 are in an intimate relationship. However, the inventors of the present invention clearly showed that caspase-14 has considerably different characteristics. The inventors of the present invention determined for the first time that SCCA-1 is an intrinsic inhibitor against caspase-14. The most unique characteristic of SCCA-1 is its remarkable specificity for caspase-14. Other members of caspase-1 to −10 are not affected by SCCA-1. SCCA-1 did not inhibit caspase-3 activity using the synthetic substrate DEVD-MCA or the natural substrate ICAD. Crm A belongs to the serpin superfamily and is known to be able to inhibit a large number of caspases including caspase-1 and caspase-8 (Gagliardini, V., et al., Science 263, 826-8 (1994)). XIAP is known to inhibit caspase-3, -7 and -9 (Srinivasula, S. M., et al., Nature 410, 112-6 (2001)). Since the anti-apoptotic protein p35 inhibits caspase-1, -3, -6, -7, -8 and -10, it is considered to have a broader spectrum. The fact that all of these inhibitory proteins consisting of Crm A, IAP and p35 are able to inhibit a portion of several initiator and effector caspases suggests that these molecules are involved in execution of the typical apoptosis pathway. On the other hand, the results obtained by the inventors of the present invention also strongly suggest that, although SCCA-1 is not a key factor in ordinary apoptotic phenomena, it is an important regulator in the denucleation process mediated by caspase-14.

The molecular mechanism of this process has yet to be elucidated. The inventors of the present invention clearly demonstrated that human caspase-14 is able to decompose ICAD in the presence of cosmotropic salt. ICAD (also referred to as DNA fragmentation factor DFF45) is an inhibitor of a magnesium-dependent endonuclease referred to as caspase-activated DNase (CAD) (or DFF40). The ICAD/CAD system plays an important role in the decomposition of chromosomal DNA during apoptotic cell death. ICAD bound to CAD is present in the form of an inactive complex. Caspase-3 exhibits limited protein decomposition against ICAD, cleaving at the two sites of $Asp^{117}$ and $Asp^{224}$. This cleavage activates CAD and initiates DNA decomposition (Nagata, S., Exp. Cell Res., 256, 12-8 (2000)). Although caspase-3 is not necessarily required for cleavage of a large number of cellular proteins during apoptosis, it is essential for cleaving ICAD (Tang, D., et al., J. Biol. Chem., 273, 28549-52 (1998)). This indicates that caspase-3 is extremely important for DNA fragmentation, while other effector caspases such as caspase-6 and caspase-7, are not important. Interestingly enough, caspase-14 formed fragments resembling 12 KDa and 35 KDa from ICAD. Sequence analysis indicated identical cleavage sites. This suggests that caspase-14 can be a perfect substitute for caspase-3. Although caspase-14 is able to decompose ICAD, it is clearly different from pro-apoptotic caspase-3 for the reasons indicated below. Firstly, excessive expression of caspase-14 does not induce apoptotic cell death (Van de Craen, Cell Death Differ., 5, 838-46 (1998)). This characteristic is in contrast with that of caspase-3. Secondly, caspase-14 is not activated by various apoptotic stimuli (Lippens, et al. (2000), op cit). Initiator caspase and other caspase members were unable to process pro-caspase-14. This finding agrees with previous findings (Lippens, et al. (2000), op cit). Thirdly, synthesis of caspase-14 is limited to differentiating keratinocytes in adult tissue (Eckhart, L., Biochem. Biophys. Res. Commun., 277, 655-9 (2000)). In addition, the ability of caspase-14 with respect to ICAD cleavage is regulated by a mechanism that is considerably different from caspase-3. Decomposition of ICAD by caspase-14 requires an abnormally high concentration of cosmotropic ion. Other caspases demonstrated hardly activity at this ion concentration. Overall, since the activation of caspase-14 is regulated by a keratinocyte differentiation program, it is considered to have a unique position among members of the caspase family.

Involvement of the ICAD/CAD system in terminal differentiation of keratinocytes is further supported by in vivo experiments. Immunohistochemical research has shown that ICAD is present in the nuclei of basal keratinocytes to spinous keratinocytes, is not present in granular cells, and that the disappearance of nuclei occurs at the time of terminal differentiation. Strong staining of ICAD has been demonstrated at porphyritic sites in the superficial epidermis of AD patients. These areas have slightly coarse surfaces and low translucency. Groups of PI-positive, undigested nuclei were present locally at these areas. Other areas were not stained with anti-ICAD antibody. In addition, although tape stripping tests performed on the skin of AD patients revealed the presence of intact ICAD protein, this was not detected in extracts from normal subjects. These results suggest that ICAD is involved in the denucleation process at the time of terminal differentiation.

There is hardly any expression of SCCA-1 in normal skin. On the other hand, SCCA-1 is strongly expressed in psoriatic skin, mucous membranes and the esophagus (Takeda, A., et al., J. Invest. Dermatol., 118, 147-54 (2002)). Interestingly enough, these tissues are accompanied by parakeratosis. The inventors of the present invention clearly demonstrated strong staining of SCCA-1 is also found at sites of parakeratosis. Moreover, SCCA-1 and ICAD were always present locally at the same sites as sites where groups of nuclei were present. Since there were no other areas of the skin surface where SCCA-1 or ICAD is negative, the co-localization of these molecules at parakeratotic sites suggests that these molecules are involved in inhibition of the denucleation process. Nuclei were reported not to disappear in a skin-equivalent model due to the pan-caspase inhibitor VAD-FMK (Weil, et al., 1999). The finding of the inventors of the present invention that VAD-FMK is one of the most potent caspase-14 inhibitors enhances the possibility that caspase-14 is probably a candidate for this reaction. Caspase-14 is down-regulated at parakeratotic sites of psoriatic skin, and is not present in epidermis of the oral cavity. In epidermis of the oral cavity, the disappearance of nuclei is either lost in some form, or is simply not carried out (Lippens, et al. (2000) op cit). Interestingly enough, SCCA-1 is up-regulated in these tissues. Most likely the abnormal expression of these molecules causes incomplete differentiation, including the permanent presence of nuclei.

The mechanism by which caspase-14 is activated in the skin is not fully understood. Activation is only observed in skin or a skin-equivalent model, and is not observed in cultured cells (Eckhart, L., et al. (2000) op cit). The inventors of the present invention actually tested this under various conditions. These conditions included addition of serum, prolongation of the duration of culturing to day 14 in the presence or absence of calcium after the cells became dense, treatment by calcium ionophore A23187, and exposure to air for 30 minutes, which is adequate for up-regulating numerous differentiation markers. Although these differentiation stimuli induced prominent expression of caspase-14 mRNA, they were not effective for inducing caspase-14 activity (data not shown). The activation process is strictly controlled and is strongly inhibited in monolayer cultures. Layering and exposure to air are thought to be required for activation. It is clear that control of activation of caspase-14 is not mediated by an apoptosis program, but rather mediated by a differentiation program. During the terminal differentiation process, numerous proteinases are activated, including serine, cysteine and aspartic acid proteinases. Trypsin-like and chymotrypsin-like serum proteinases are suggested to fulfill the role of exfoliating the outermost keratinocytes. Some cysteine proteinases, such as cathepsin B and L, are up-regulated in differentiated keratinocytes. Cathepsin D and aspartic acid proteinase are also suggested to fulfill the role of exfoliating keratinocytes. These enzymes may also be involved in other differentiation mechanisms such as the activation of caspase-14.

In summary of the above, the inventors of the present invention purified caspase-14 from human keratinocyte extract. Although caspase-14 induces disappearance of nuclei and their disappearance resembles apoptosis, it is strongly suggested to be a distinguishable change that occurs mediated by decomposition of ICAD in the final stage of keratinocyte differentiation. Although this process shares several apoptotic factors, it does not involve cell death leading to elimination of damaged cells, but rather is a constitutional process for the purpose of completing overall structure to demonstrate the primary role in the form of a barrier function. Abnormal expression of caspase-14 or SCCA-1 has a direct effect on the differentiation program and as a result, leads to the occurrence of parakeratosis and a breakdown of the barrier function.

(2-xiv) Screening Method

Screening for substances that inhibit parakeratosis was carried out in the manner described below. The herbal medicines indicated below were tested.

Cattail extract (Ichimaru Pharcos Co., Ltd.)
Grape extract (Ichimaru Pharcos Co., Ltd.)
Tomato extract (Ichimaru Pharcos Co., Ltd.)
Cucumber extract (Ichimaru Pharcos Co., Ltd.)
Kiwi extract (Ichimaru Pharcos Co., Ltd.)
Jujube extract ((Ichimaru Pharcos Co., Ltd.)
Tormentilla (Ichimaru Pharcos Co., Ltd.)

(a) Measurement of Cysteine Protease Enzyme Activity

80 μl of assay buffer (50 mM HEPES (pH 7.5)), 5 mM DTT, 2.5 mM EDTA and 0.1% CHAPS) and 20 μl of 1 μg/ml papain (Sigma) were mixed and incubated for 15 minutes at room temperature. Next, 20 μl of 2.5 mM Nα-benzoyl-L-arginine 4-nitroanilide hydrochloride (L-BAPNA) substrate were added followed by incubating for 15 minutes at 37° C. 30 μl of a 25% acetic acid solution in ethanol and 30 μl of 0.2% p-dimethylaminocinnamaldehyde were added thereto to develop color followed by measurement of absorbance at 545 nm. This absorbance was defined as the enzyme activity [x] of cysteine protease.

(b) Measurement of Enzyme Activity of System Containing Candidate Herbal Medicine for Inhibiting Parakeratosis and Cysteine Protease 60 μl of the aforementioned assay buffer and 20 μl of candidate substance were incubated for 30 minutes at room temperature. 20 μl of 1 μg/ml papain were added thereto followed by incubating for 15 minutes at room temperature. Next, 20 μl of 2.5 nM L-BAPNA were added followed by incubating for 15 minutes at 37° C. 30 μl of a 25% acetic acid solution in ethanol and 30 μl of 0.2% p-dimethylaminocinnamaldehyde were added to develop color followed by measurement of absorbance at 545 nm. This absorbance was defined as the enzyme activity of cysteine protease [y], the percentage (%) of each tested compound with respect to the aforementioned [x] is shown in the column entitled "Sample only" in the following Table 2.

The values shown in the "Sample only" column serve as indicators of the cysteine protease inhibitory activity of the tested herbal medicines per se, or in other words, the closer that value is to 100, the lower the cysteine protease inhibitory activity of the test herbal medicine. In addition, the values of [100-[sample only]], obtained by subtracting the value of "sample only" from 100, are also shown in Table 2. In this case, the closer that value is to zero, the lower the cysteine protease inhibitory activity of the tested herbal medicine.

(c) Measurement of Enzyme Activity of System Containing SCCA-1, Candidate Herbal Medicine and Cysteine Protease 40 μl of the aforementioned assay buffer and 20 μl of recombinant SCCA-1 were mixed followed by the addition of 20 μl of a candidate herbal medicine and incubating for 30 minutes at room temperature. 20 μl of 1 μg/ml papain were then added thereto followed by incubating for 15 minutes at room temperature. Next, 20 μl of 2.5 mM L-BAPNA were added followed by incubating for 15 minutes at 37° C. 30 μl of 25% acetic acid solution in ethanol and 30 μl of 0.2% p-dimethylamino-cinnamaldehyde were added to develop color followed by measurement of absorbance at 545 nm. This absorbance was defined as the enzyme activity [z] of cysteine protease, and percentage (%) of each tested substance with respect to the aforementioned [x] is shown in the column entitled "SCCA-1+" in the following Table 2.

The value of "SCCA-1+" is an indicator of the total cysteine protease inhibitory activity of SCCA-1 and the cysteine protease inhibitory activity of the tested herbal medicine per se, or in other words, the closer that value is to 100, the lower the total inhibitory activity thereof.

In addition, the column entitled "Difference" in the table indicates the value obtained by subtracting the value of "Sample only" from the value of "SCCA-1+". A large difference indicates that the cysteine protease inhibitory activity of SCCA-1 in the system containing SCCA-1, candidate herbal medicine and cysteine protease is low. In other words, this suggests that suppression of the cysteine protease inhibitory activity of SCCA-1 by the candidate herbal medicine is remarkable.

The results are summarized in Table 2 below.

TABLE 2

| Extract | [SCCA-1+] | [Sample only] | 100-[Sample only] | [Difference] |
|---|---|---|---|---|
| Kiwi | 16.6 | 88.0 | 12.0 | 4.6 |
| Cucumber | 12.2 | 92.7 | 7.3 | 5.0 |
| Jujube | 14.2 | 88.8 | 11.2 | 3.1 |
| Tomato | 13.3 | 92.7 | 7.3 | 6.0 |
| Cattail | 49.8 | 66.5 | 33.5 | 16.3 |
| Grape | 24.9 | 83.9 | 16.1 | 8.8 |
| Tormentilla | 10.3 | 2.3 | 97.7 | −87.3 |

As a result, cattail extract, grape extract, tomato extract, cucumber extract, kiwi extract and jujube extract, and particularly cattail extract, were found to significantly suppress the cysteine protease inhibitory activity of SCCA-1. Thus, these extracts are expected to be effective in inhibiting epidermal parakeratosis.

INDUSTRIAL APPLICABILITY

According to the present invention, a method and pharmaceutical composition are provided for treating and/or preventing a disease selected from the group consisting of psoriasis and squamous cell carcinoma. In addition, according to the present invention, a means for inhibiting and treating epidermal parakeratosis can be provided that uses a completely novel approach differing from the prior art.

The invention claimed is:

1. A method for treatment and/or prevention of a disease selected from the group consisting of psoriasis and squamous cell carcinoma by inhibiting the expression of squamous cell carcinoma antigen (SCCA) by cells, wherein the inhibition of the expression of SCCA by cells is carried out by RNA interference of a gene encoding SCCA, and wherein the RNA interference uses a double-stranded RNA comprising a sense oligonucleotide strand containing the oligonucleotide of SEQ ID NO. 1 or mutant thereof and an antisense oligonucleotide strand containing the oligonucleotide of SEQ ID NO. 2 or mutant thereof.

* * * * *